(12) United States Patent
Marban et al.

(10) Patent No.: US 8,003,618 B2
(45) Date of Patent: Aug. 23, 2011

(54) FOCAL CALCIUM CHANNEL MODULATION

(75) Inventors: Eduardo Marban, Beverly Hills, CA (US); Mitsushige Murata, Tokyo (JP)

(73) Assignee: The John Hopkins University, Baltimore, MD (US)

( * ) Notice: Subject to any disclaimer, the term of this patent is extended or adjusted under 35 U.S.C. 154(b) by 1434 days.

(21) Appl. No.: 10/678,723

(22) Filed: Oct. 2, 2003

(65) Prior Publication Data

US 2004/0204376 A1 Oct. 14, 2004

Related U.S. Application Data

(60) Provisional application No. 60/415,649, filed on Oct. 2, 2002.

(51) Int. Cl.
*A01N 63/00* (2006.01)
*A61K 48/00* (2006.01)
(52) U.S. Cl. ..................... 514/44 R; 424/93.1
(58) Field of Classification Search .................. 514/16.4, 514/44 R; 424/93.1
See application file for complete search history.

(56) References Cited

U.S. PATENT DOCUMENTS

| | | |
|---|---|---|
| 5,163,950 A | 11/1992 | Pinchuck et al. |
| 5,436,128 A | 7/1995 | Harpold et al. |
| 5,662,585 A | 9/1997 | Willis et al. |
| 5,824,550 A | 10/1998 | Hruska et al. |
| 5,836,905 A | 11/1998 | Lemelson et al. |
| 5,944,710 A | 8/1999 | Dev et al. |
| 5,965,396 A | 10/1999 | Pan et al. |
| 6,086,582 A | 7/2000 | Altman et al. |
| 6,156,726 A | 12/2000 | Newcomb et al. |
| 6,207,422 B1 | 3/2001 | Brown et al. |
| 6,214,620 B1 | 4/2001 | Johns et al. |
| 6,309,375 B1 | 10/2001 | Glines et al. |
| 6,365,337 B1 | 4/2002 | Letts et al. |
| 6,605,274 B1 | 8/2003 | Dillmann et al. |
| 6,776,987 B1 | 8/2004 | Edelberg et al. |
| 7,122,307 B2 | 10/2006 | Rosen et al. |
| 2002/0009772 A1 | 1/2002 | Snutch |
| 2002/0094326 A1 | 7/2002 | Donahue et al. |
| 2002/0155101 A1 | 10/2002 | Donahue et al. |
| 2002/0187949 A1 | 12/2002 | Rosen et al. |
| 2002/0188212 A1 | 12/2002 | Rosen et al. |
| 2003/0118988 A1 | 6/2003 | Kandel et al. |
| 2003/0195470 A1 | 10/2003 | Ponzi |
| 2004/0204376 A1 | 10/2004 | Marban et al. |
| 2004/0254134 A1 | 12/2004 | Marban et al. |
| 2005/0074850 A1 | 4/2005 | Nadler et al. |
| 2007/0042347 A1 | 2/2007 | Rosen et al. |
| 2009/0291068 A1 | 11/2009 | Marban et al. |

FOREIGN PATENT DOCUMENTS

| | | |
|---|---|---|
| WO | 99/23880 | 5/1990 |
| WO | 96/28537 | 9/1996 |
| WO | 99/32615 | 7/1999 |
| WO | 00/18903 | 4/2000 |
| WO | 00/38518 | 7/2000 |
| WO | 00/41731 | 7/2000 |
| WO | 02/19966 | 3/2002 |
| WO | 02/33111 | 4/2002 |

OTHER PUBLICATIONS

Concalves M, A concise peer into the background, initial thoughts, and practices of human gene therapy, 2005, BioEssays, vol. 27, pp. 506-517.*
Parekh-Olmedo H, Gene therapy progress and prospects: targeted gene repair, 2005, Gene Therapy, vol. 12, pp. 639-646.*
Verma IM, Gene Therapy: Twenty-first century medicine, 2005, Annu. Rev. Biochem. vol. 74, pp. 711-738.*
Fishbein I, Site specific gene delivery in the cardiovascular system, 2005, J. Controlled Release, vol. 109, pp. 37-48.*
Wright et al., 2001, Basic Res. Cardiol., vol. 96, pp. 227-236.*
Beguin et al., 2001, Nature, vol. 411, pp. 701-706.*
Lipscombe D., 2002, Circulation Res., vol. 90(9), pp. 981-987.*
Elliott, 2001, Cell Calcium, vol. 30(2), pp. 72-93.*
Krougliak et al., 2001, J Gene Med., vol. 3, pp. 51-58.*
Li et al., 2001, Cancer Research, vol. 61, pp. 6428-6236.*
Maguire et al., 1994, Science, vol. 265, pp. 241-244.*
Finlin et al., 2000, Biochem J., vol. 347, pp. 223-231.*
Liu et al., 2007, J. Gene Med., vol. 9, pp. 613-619.*
Murata et al., 2004, Cir. Res., vol. 95, pp. 398-405.*
Ballipejalli et al., 2004, Cir. Res., vol. 95, pp. 337-339.*
Aresta, S. et al., "A Novel Rho GTPase-activating-protein interacts with Gem, a member of the Ras superfamily of GTPases," *Biochem. J.*, 2002, pp. 57-65. vol. 367.
Muth, James N. et al., "Use of transgenic mice to study voltage-dependent $Ca^{2+}$ channels," *Trends in Pharmacological Sciences*, Oct. 2001, pp. 526-532. vol. 22. No. 10.
Dunlap, K. et al., "Exocytotic $Ca^{2+}$ Channels in Mammalian Central Neurons," *Trends Neurosci.*, 1995, vol. 18. p. 89.
Fisher, R. et al.., "Calmodulin Binds to and Inhibits GTP Binding of the Ras-like GTPase Kir/Gem," *Journal Biology Chemistry*, 1996, vol. 271. pp. 2506-2507.
Zaritsky et al., "Targeted Disruption of Kir2.1 and Kir2.2 Genes Reveals the Essential Role of the Inwardly Rectifying K+ Current in K+ Mediated Vasodilation" (2000) Circ. Res. 87:160-166.
Nuss HB et al. "Overexpression of a Human Potassium Channel Suppresses Cardiac Hyperexcitability in Rabbit Ventricular Myocytes" (1999) JCI 103(6):889-896.
Nuss HB et al., "Reversal of Potassium Channel Deficiency in Cells From Failing Hearts by Adenoviral Gene Transfer; A Prototype for Gen Therapy for Disorders of Cardiac Excitability and Contractility" (1996) Gene Therapy 3 (3):900-912.

(Continued)

*Primary Examiner* — Peter Paras, Jr.
*Assistant Examiner* — David Montanari
(74) *Attorney, Agent, or Firm* — Banner & Witcoff, Ltd.

(57) ABSTRACT

Disclosed is an invention for focally modulating the activity of a calcium channel in a mammal. In one aspect, the invention features a method that includes contacting a pre-determined tissue or organ region with a nucleic acid sequence encoding a GEM protein or a variant thereof to express the GEM protein or variant within the region. Typical methods further include expressing the GEM protein or variant so as to modulate the activity of the calcium channel. The invention has a wide spectrum of useful applications including treating a medical condition associated with unsuitable calcium channel activity.

27 Claims, 9 Drawing Sheets

OTHER PUBLICATIONS

Plaster et al., "Mutation in Kir 2.1 Cause the Developmental and Episodic Electrical Phenotypes of Anderson's Syndrome" (2001) Cell 105:511-519.

Plotinikov, AN, "Biological Pacemaker Implanted in Canine Left Bundle Branch Provides Ventricular Escape Rhythms That Have Physiologically Acceptable Rates" (2004) Circulation 109: 506-512.

Proenza et al., "Pacemaker Channels Produce and Instantaneous Current" (2002) JBC 277(7):5101-5109.

Rosen, MR et al., "Genes, Stem Cells and Biological Pacemakers" (2004) Cardiovasc. Res. V. 64(1):12-23.

Saffitz et al., "Mechanisms of Remodeling of Gap Junction Distributions and the Development of Anatomic Substrates of Arrhythmias" (1999) Cardiovasc Res. 42:309-317.

Schroder "Gene Delivery Approaches to Heart Failure Treatment" (2004) Expert Opin. Biol. Ther. 4(9):1413-1422.

Sehareseyon J et al., "Molecular Composition of Mitochondrial ATP-Sensitive Potassium Channels Probed by Viral Kir Gene Transfer" (2000) J. Mol. Cell. Cardiol. 32:1923-1930.

Sobey et al., "Knockout Blow for Channel Identity Crisis Vasodilation to Potassium is Mediated Via Kir2.1" (2000) Circ. Res. 87:83-84.

Sugiyama A et al., "Measurement of Adenylyl Cyclase Activity in the AV Nodal Region of the Canine Heart: Evidence for Inhibition by Adenosine and Acetylcholine" (1997) J. of Cardiovasc. Pharm. vol. 29, pp. 734-739.

Swifka et al., "Epicardial Fat From Guinea Pig: A Model to Study the Paracrine Network of Interactions Between Epicardial Fat and Myocardium?" (2008) Cardiovasc. Drugs and Ther. 22:107-114.

Tinker et al., "Regions Responsible for the Assembly of Inwardly Rectifying Potassium Channels" (1996) Cell 87:857-868.

Tiritilli, A., "DOCA-Salts Induce Heart Failure in the Guinea Pig" (2001) Eur. J. of Heart Fail. 3:545-551.

Tomaselli GF et al., "Electrophysiological Remodeling in Hypertrophy and Heart Failure" (1999) Cardiovascular Res. 42:270-283.

Weimann, JM et al, "Stable Reprogrammed Heterokaryons Form Spontaneously in Purkinje Neurons After Bone Marrow Transplant" (2003) Nature Cell Biol. 5(11):959-966.

Xue T et al., "Dominant-Negative Suppression of HCN-1 and HCN-2-Encoded Pacemaker Current by an Engineered HCN1 Construct (Insights Into Structure-Function Relationships and Mulitmerization)" (2002) Circ. Res. 90:1267-1273.

Xue T et al., "Functional Integration of Electrically Active Cardiac Derivatives From Genetically Engineered Human Embryonic Stem Cells With Quiescent Recipient Ventricular Cardiomyocytes" (2005) Circulation 111(1): 11-20.

Yamagishi T et al., "Molecular Architecture of the Voltage-Dependent NA Channel: Functional Evidence for Helicase in the Pore" (2001) J. Gen Phys. 118:171-181.

Yla-herttuala, "Cardiovascular Gene Therapy" (2000) Lancet 355:213-222.

Marban, "Cardiac Channelopathies", Nature, Jan. 10, 2002, pp. 213-218, vol. 415.

Maguire et al., "Gem: An Induced, Immediate Early Protein Belonging to the Ras Family", Science, Jul. 8, 1994, vol. 265.

Leone et al., "The Gem GTP-binding Protein Promotes Morphological Differentiation in Neuroblastoma", Oncogene, pp. 3217-3225, vol. 20, 2001.

Neyroud et al., "Gene Delivery to Cardiac Muscle", Methods in Enzymology, pp. 323-334, vol. 346, 2002.

Marban et al., "Gene Therapy for Cardiac Arrhythmias", Cold Spring Harbor Symposia on Quantitative Biology, 2002, vol. LXNII.

Miake et al., "Biological Pacemaker Created by Gene Transfer", Nature, Sep. 12, 2002, pp. 132-133, vol. 419.

Dolphin, "Mechanisms of Modulaton of Voltage-Dependent Calcium Channels by G Proteins", Journal of Physiology, 1998, pp. 3-11, vol. 506.1.

Ertel, "Nomenclature of Voltage-Gated Calcium Channels", Neuron, Mar. 2000, pp. 533-535, vol. 25.

Beguln et al., "Regulation of $Ca^{2+}$ Channel Expression at the Cell Surface by the Small G-protein kir/Gem", Nature, Jun. 7, 2001, pp. 701-706, vol. 411.

Catterall, "Structure and Regulation of Voltage-Gated $Ca^{2+}$ Channels", Annual Rev. Cell Dev. Biology, 2000, pp. 521-555, vol. 16.

Walker et al., "Subunit Interaction Sites in Voltage-Dependent $Ca^{2+}$ Channels: Role in Channel Function", Elsevier Science, Ltd., 1998, pp. 148-154, vol. 21.

Trimmer, "Unexpected Cross Talk: Small GTPase Regulation of Calcium Channel Trafficking", Science's Stke, Jan. 8, 2002, pp. 1-3.

Accili et al., "From Funny Current to HCN Channels: 20 Years of Excitation" (2002) News Physiol. Sci. 17:32-37.

Akhter SA et al., "Restoration of B-Adrenergic Signaling in Failing Cardiac Ventricular Myocytes Via denoviral-Mediated Gene Transfer" (1997) PNAS 94:12100-12105.

Bannister et al, "Conserved Extracellular Cysteine Residues in the Inwardly Rectifying Potassium Channel Kir2.3 Are Required for Function But Not Expression in the Membrane" (1999) FEBS Letters 485(3):393-99.

Bauer A et al., "Inhibitory G Protein Expression Provides Physiologically Relevant Heart Rate Control in Persistent Atrial Fibrillation" (2004) Circulation 110:3115-3120.

Brown, "Regulation of Heartbeat by G Protein-Coupled Ion Channels" (1990) Am J. Phys. 259(6):H1621-1628.

Campbell et al., "Therapeutic Drug Monitoring: Antiarrhythmic Drug" (1998) Br J Clin. Pharmacol. 46:307-319.

Chen et al., "Lack of Muscarinic Regulation of Ca2+ Channels in Gi2alpha Gene Knockout Mouse Hearts" (2001) Am. J. Physiol 280: H1989-H1995.

Chiang CE et al., "The Long QT-Syndrome: Genetic Basis and Clinical Implications" (2000) J. Amer. Coll. Cardiol. 36 (1):1-12.

Cho et al., "Creation of a Biological Pacemaker by Cell Fusion" (2007) Circ. Res. 100 (8):1112-1115.

Donahue JK, "Gene Therapy for Cardiac Arrhythmias" (2004) Ann. NY Acad. Sci., 1015: 332-337.

Donahue JK et al., "Focal Modification of Electrical Conduction in the Heart by Viral Gene Transfer" (2000) Nat. Med. 6(2): 1395-1398.

Donahue JK et al., "Gene Therapy for Cardiac Arrhythmias" (2005) Trends Cardiovasc. Med. 15:219-224.

Donahue JK et al., "Gene Transfer Techniques for Cardiac Arrhythmias" (2004) Ann. Med. 36(supp 1): 98-105.

Donahue JK et al., "Ultrarapid, Highly Efficient Viral Gene Transfer to the Heart" (1997) PNAS 94:4664-4668.

Donahue, JK et al. "Acceleration or Widespread Adenoviral Gene Transfer to Intact Rabbit Hearts by Coronary Perfusion With Low Calcium and Serotonin" (1998) Gene Therapy 5:630-634.

DuBrow et al., "Comparison of Cardiac Refractory Periods in Children and Adults" (1975) Circulation 51:485-491.

Edelberg JM, "Enhancement for Murine Cardiac Chronotropy by the Molecular Transfer of the Human Bets2 Adrenergic Receptor cDNA" (1998) JCI 101:337-343.

Ennis et al., "Dual Gene Therapy With SERCA1 and Kir2.1 Abbreviates Excitation Without Suppressing Contractility" (2002) JCI 109(3) 393-400.

Er et al., "Dominant-Negative Suppression of HCN Channels Markedly Reduces the Native Pacemaker Current (It) and Undermines Spontaneous Beating of Neonatal Cardiomyocytes" (2003) Circulation 107:485-489.

Fink et al., "Dominant-Negative Chimeras Provide Evidence for Homo and Heteromultimeric Assembly of Inward Rectifier K+ Channels Proteins Via Their N-Terminal End" (1996) FEBS Letters 378(1) 64-68.

French BA et al., "Direct in Vivo Gene Transfer Into Porcine Myocardium With Replication-Deficient Adenoviral Vectors" (1994) Circulation 90(5):2414-2424.

Glenn CM et al., "Gene Therapy to Develop a Genetically Engineered Cardiac Pacemaker," (2003) J. Cardiocvasc. Nurs. 18:330-336.

Gros DB et al., "Connexins in Mammalian Heart Function" (1996) Bioessays 18(9):719-730.

Hadcock, JR et al., "Cross-Regulation Between G-Protein-Mediated Pathways" (1990) JBC 265(25): 14784-14790.

Hajjar RJ et al., "Prospects for Gene Therapy for Heart Failure" (2000) Circ. Res. 86(6) 616-621.

Hasenfuss, G., "Animal Models of Human Cardiovascular Disease, Heart Failure, and Hypertrophy" (1998) Cardiovascular Research 39:60-76.

*Homo sapiens* Hyperpolarization Activated Cyclic Nucleotide-Gated Potassium Channel (HCN1) mRNA complete coding sequence, Database EMBL [online], EMBL: AF488549, 2003.

Hoppe et al., "Distinct Gene-Specific Mechanisms of Arrhythmia Revealed by Cardiac Gene Transfer of Two Long-QT Disease Genes HERG and KCNE1" (2001) PNAS USA 98(9): 5335-5340.

Hoppe et al., "Adenovirus-Mediated Inducible Gene Expression in Vivo by a Hybrid Ecdysone Receptor" (2000) Mol. Ther. 1(2):159-164.

Hoppe et al., "Molecular Dissection of Cardiac Repolarization by in Vivo Kv4.3 Gene Transfer" (2000) JCI 105 (8):1077-1084.

Hoppe, UC et al., "Manipulation of Cellular Excitability by Cell Fusion: Effects of Rapid Introduction of Transient Outward K+ Current on the Guinea Pig Action Potential" (1999) Circ. Res. 84(8):964-972.

Johns DC et al., "Suppression of Neuronal and Cardiac Transient Outward Currents by Viral Gene Transfer of Dominant-Negative Kv4.2 Constructs" (1997) JBC 272(50): 34598-31603.

Johns et al. "Adenovirus-Mediated Expression of a Voltage-Gated Potassium Channel in Vitro (Rat Cardiac Myocytes) and in Vivo (Rat Liver). A Novel Strategy for Modifying Excitability" (1995) JCI 96:1152-1158.

Kashiwakura, Y. et al., "Gene Transfer of a Synthetic Pacemaker Channel Into the Heart: A Novel Strategy for Biological Pacing" (2006) Circulation, vol. 114 (16):1682-1686.

Kass-Eiser et al., "Quantitative Determination of Adenovirus-Mediated Gene Delivery to Rat Cardiac Myocytes in Vitro and in Vivo" (1993) PNAS 90:11498-11502.

Kickuchi K et al., "Targeted Modification of Atrial Electrophysiology by Homogenous Transmural Atrial Gene Transfer" (2005) Circulation 111: 264-270.

Lalli MJ et al., "Sarcoplasmic Reticulum Ca-ATPase (SERCA) la Structurally Substitutes for SERCA 2a in the Cardiac Sarcoplasmic Reticulum and Increases Cardiac Ca2+ Handling Capacity" (2001) 89:160-167.

Lawrence JH et al., "Prospects for Genetic Manipulation of Cardiac Excitability" (1995) Adv. In Exper. Med. and Biol. 382:41-48.

Murata et al., "Creation of a Genetic Calcium Channel Blocker by Targeted GEM Gene Transfer in the Heart" (2004) Circ Res 95:398-405.

Lerman, BB et al., "Mechanism of Repetitive Monomorphic Ventricular Tachycardia" (1995) Circulation 92:421-429.

Li et al., "Evidence for Two Components of Delayed Rectifier K Current in Human Ventricular Myocytes" (1996) Circulation Research 78:689-696.

Lopatin An et al., "Inward Rectification and Cardiac Excitability" (2002) Biologicheskie Membrany 19(1):57-65.

Lu et al., "Density and Kinetics of Ikr and Iks in Guinea Pig and Rabbit Ventricular Myocytes Explain Different Efficacy of Iks Blockade at High Heart Rate in Guinea Pig and Rabbit: Implications for Arrhythmogenesis in Humans" (2001) Circulation 104:951-956.

Marban E et al., "Biological Pacemakers as a Therapy for Cardiac Arrhythmias" (2008) Curr. Opinion in Cardiol. 23(1):46-54.

Marban E., "Circulation Research Impact Factor Sets New Record" (2001) Circ. Res. 89:101.

Marban, E et al., "Creation of a Biological Pacemaker by Gene- or Cell-Based Approaches" (2007) Med. Bio. Eng. Comput. 45:133-144.

Mazhari R et al., "Molecular Interactions Between Two Long-QT Syndrome Gene Products, HERG and KCNE2, Rationalized by in Vitro and in Silico Analysis" (2001) Circ. Res. 89:33-38.

Muhlhauser J et al., "Safety and Efficacy of in Vivo Gene Transfer Into the Porcine Heart With Replication-Deficient, Recombinant Adenovirus Vectors" (1996) Gene Therapy 3:145-153.

Mullins, FM et al., "Functional Interaction Between Extracellular Sodium, Potassium and Inactivation Gating in HERG Channels" (2004) J Physiol., V. 558(3):729-744.

Nakamura et al., "Inhibition of Rat Ventricular IK1 With Antisense Oligonucleotides Targeted to Kir2.1 mRNA" (1998) Am. J. Phys. 274(3)(2):H892-H900.

\* cited by examiner

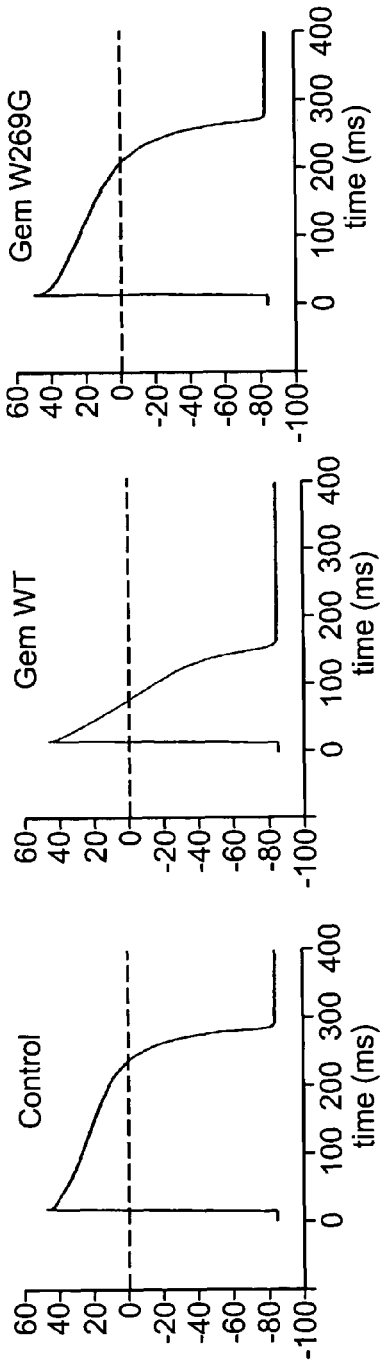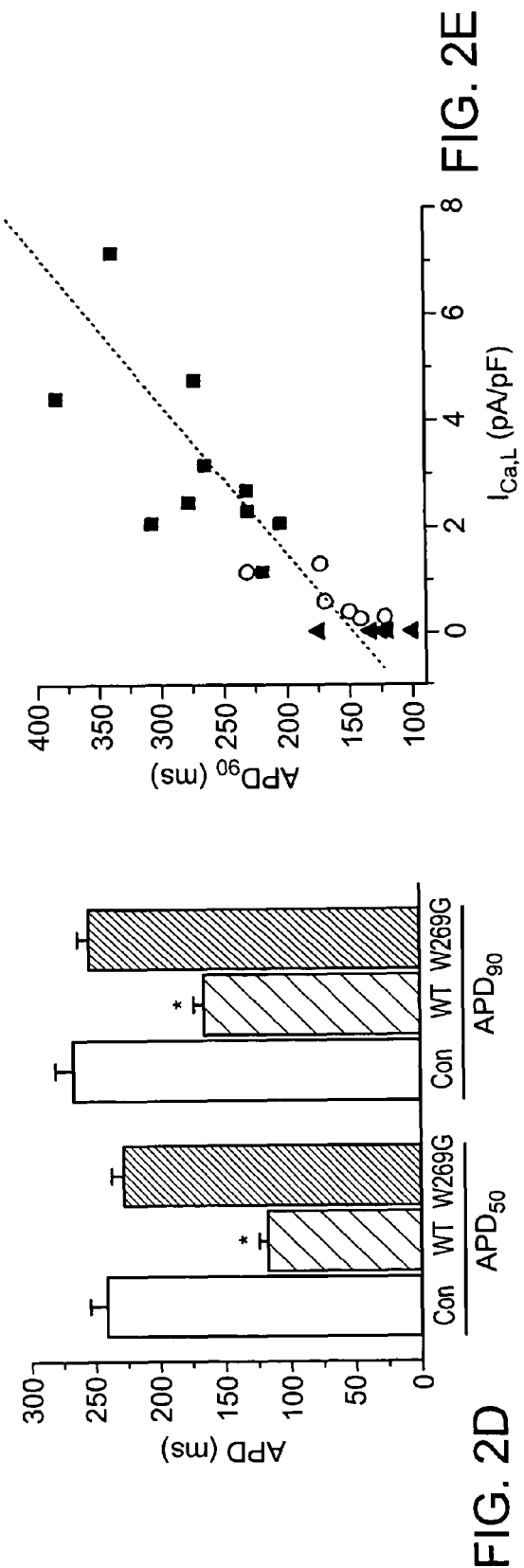

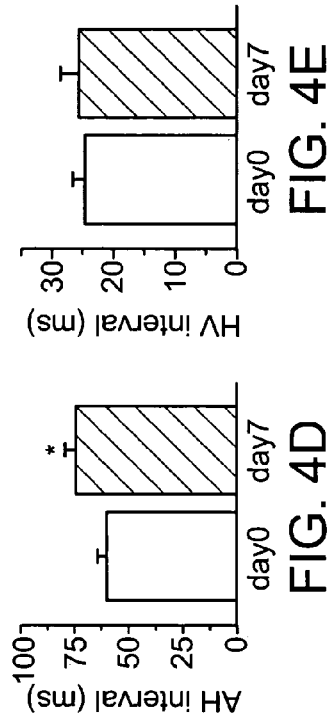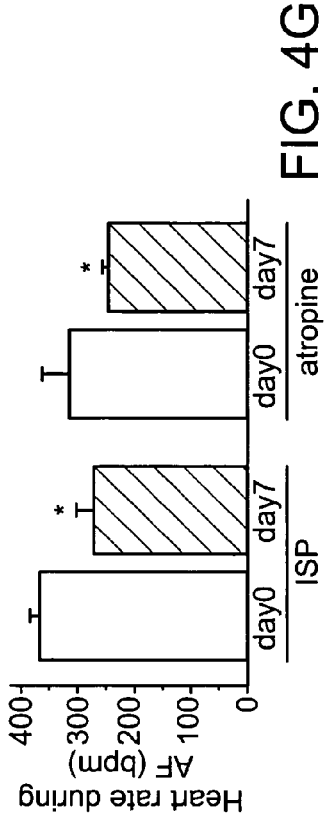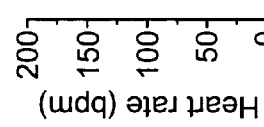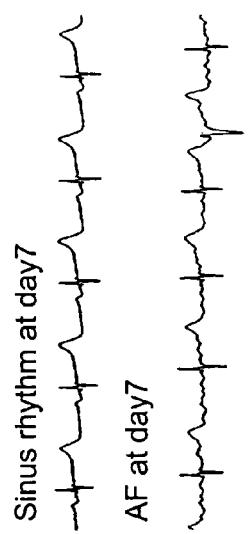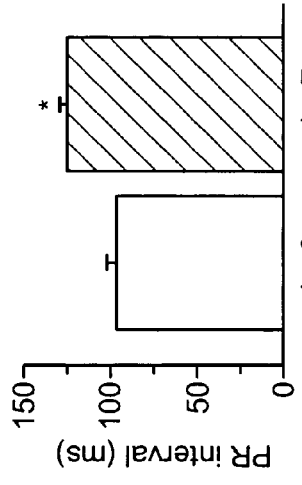
FIG. 4A
FIG. 4B
FIG. 4C
FIG. 4D
FIG. 4E
FIG. 4F
FIG. 4G Left ventricular function of βgal- and W269G-transduced mice after sham operation or TAC

| Parameter | sham | βgal+TAC | W269G+sham | W269G+TAC |
|---|---|---|---|---|
| Number | 10 | 7 | 4 | 7 |
| Heart rate (bpm) | 579 ± 11 | 590 ± 9 | 549 ± 13 | 530 ± 23 † |
| Systolic | | | | |
| ESLVP (mmHg) | 84.0 ± 1.9 | 145 ± 2.3* | 81.7 ± 3.9 | 141 ± 6.9 |
| ESV (μl) | 12.6 ± 1.0 | 4.5 ± 0.5 * | 19.1 ± 1.8 | 7.4 ± 1.8 |
| EDV (μl) | 30.8 ± 1.1 | 19.6 ± 2.2 * | 37.4 ± 2.6 | 26.4 ± 2.7 |
| EF (%) | 59.2 ± 2.8 | 77.4 ± 1.2 * | 51.3 ± 3.1 | 68.4 ± 4.7 |
| dp/dt$_{max}$ (mmHg/s) | 10620 ± 831 | 17484 ± 1006 * | 9410 ± 518 | 14936 ± 1023 |
| dp/dt$_{max}$/EDV (mmHg/s·μl$^{-1}$) | 351 ± 35 | 928 ± 69 * | 268 ± 42 | 597 ± 64 † |
| E$_{max}$ (mmHg/μl) | 6.7 ± 0.67 | 32 ± 3.5 * | 6.3 ± 0.27 | 22 ± 4.1 |
| Diastolic | | | | |
| EDLVP (mmHg) | 5.8 ± 0.7 | 9.8 ± 0.7 * | 5.4 ± 0.6 | 9.6 ± 0.7 |
| dp/dt$_{min}$ (mmHg/s) | -9362 ± 276 | -15226 ± 1045 * | -10279 ± 288 | -12697 ± 646 † |
| Tau g (ms) | 7.2 ± 0.4 | 7.7 ± 0.5 | 7.7 ± 0.4 | 9.5 ± 0.7 |

Parameters are grouped into measures of systolic (contractile) and diastolic (relaxation).
ESLVP, end-systolic left ventricular pressure; EDLVP, end-diastolic left ventricular pressure; ESV, end-systolic volume; EDV, end-diastolic volume; EF, ejection fraction; g, glantz
*, p<0.01 vs. sham group, †, p<0.05 vs. βgal+TAC group

FIG. 6

Comparison of ECG parameters at 72 h after gene delivery in control and kir/GEM-transduced animals

|  | control (n=5) | kir/GEM (n=9) |  |
|---|---|---|---|
| RR(ms) | 206.2 ± 7.4 | 214.0 ± 7.9 | NS |
| PQ(ms) | 56.2 ± 1.3 | 56.2 ± 2.5 | NS |
| QT(ms) | 159.0 ± 3.3 | 138.3 ± 3.6 | $p<0.01$ |
| QTc(ms) | 166.9 ± 1.8 | 148.2 ± 2.3 | $p<0.001$ |

FOCAL CALCIUM CHANNEL MODULATION

CROSS-REFERENCE TO RELATED APPLICATION

The present application claims priority to U.S. Provisional Application No. 60/415,649 as filed on Oct. 2, 2002 the disclosure of which is incorporated herein by reference.

STATEMENT OF U.S. GOVERNMENT INTEREST

Funding for the present invention was provided in part by the Government of the United States by virtue of Grant Nos. R37 HL36957 and P50 HL52307 from the National Institutes of Health. Accordingly, the Government of the United States has certain rights in and to the invention claimed herein.

FIELD OF THE INVENTION

Calcium channels include electrically responsive proteins with many important biological functions. The present invention provides a composition, method and system for modulating calcium channels in a focal (rather than non-specific) manner. The invention has a wide spectrum of useful applications including treating a medical condition associated with undesirable calcium channel activity.

BACKGROUND

There is general recognition that intracellular calcium ($Ca^{2+}$) plays an important role in many biological processes such as gene regulation, memory, and cell death. See Muth, J. N. et al. *Trends Pharmacol Sci* 22, 526-32 (2001); and Carafoli, E. et al. *Crit Rev Biochem Mol Biol* 36, 107-260 (2001).

More specifically, there have been reports that abnormal levels of intracellular $Ca^{2+}$ foster inappropriate calcium homeostasis in a variety of cells, tissues and organs. Cardiac and neural tissue are thought to be especially sensitive to calcium. As an illustration, certain neurons are believed to undergo abnormal neurotransmitter release, dendritic $Ca^{2+}$ transients and $Ca^{2+}$ action potentials in the presence of inadequate calcium homeostasis.

Many disorders are thought to arise or be exacerbated by inappropriate calcium homeostasis, particularly those impacting the central (CNS) and peripheral (PNS) nervous systems, as well as the endocrine and cardiovascular systems.

Voltage-gated calcium channels are thought to help control the intracellular flow of $Ca^{2+}$. These channels (also known as voltage-dependent calcium channels or VDCCs) have been disclosed as being a heterogeneous class of proteins that are responsive to depolarization. The conversion of the intracellular calcium flow by these and other channel proteins is thought to impact a wide spectrum of biological responses. See generally Catterall, W. A. *Ann. Rev. Cell Dev.* 16: 521 (2000) and U.S. Pat. No. 5,436,128.

Nearly all calcium channels are categorized as T, L, N, P, and Q types. These designations are based largely on electrophysiological and pharmacological properties of the channels. See Catterall, supra; and Dunlap, K. et al. *Trends Neurosci.* 18:89 (1995).

By way of example, L-type calcium channels are believed to be sensitive to dihydropyridine (DHP) agonists and antagonists as well as certain other compounds. The structure and function of these calcium channels have been disclosed at the molecular level. See eg., Catterall, supra; U.S. Pat. Nos. 6,365,337; U.S. Pat. Publication No. 2002009772; Perez-Reyes, E. et al. *J. Biol. Chem.* 267: 1792 (1991); and references cited therein.

See also Ertel, E. A et al. in *Neuron* 25: 533 (2000) (disclosing various voltage-gated calcium channels with reference to the molecular structure and function of these proteins).

There have been attempts to understand how L-type and other calcium channels are regulated. In this regard, a link between $_{Ca}^{2+}$ channel trafficking and certain guanosine triphosphatase enzymes (GTPases) has been reported. More specifically, interaction between some $Ca^{2+}$ channel subunits and a ras-like GTPase called Gem (also called Kir/Gem) has been disclosed.

The structure and function of Gem has been reported. See Maguire, J. et al. *Science* 265: 241 (1994) (disclosing the molecular structure of murine and human Gem proteins, for instance). It has been proposed that Gem helps prevent β subunit-mediated trafficking of $Ca^{2+}$ channels under appropriate conditions.

There is almost universal belief that the heart maintains an intrinsic rhythm by creating electric stimuli. This leads to contraction of the myocardium. These contractions are the engine that moves blood throughout the vascular system. See generally *The Heart and Cardiovascular System. Scientific Foundations*. (1986) (Fozzard, H. A. et al. eds) Raven Press, NY.

Certain channel proteins are thought to be closely linked to normal heart function. For instance, genetic mutation of some channel proteins may facilitate or at least aggravate heart disorders such as arrhythmias. As a group, such heart disorders have been referred to as "channelopathies" to denote relationship with abnormal channel protein function. See Marban, E. *Nature* 415: 213 (2002).

Abnormal channel proteins are thought to impact other heart disorders including hypertrophy, apoptosis, remodeling, fibrillation, angina and in some cases infarcts ("heart attack"). See Bers, D. M. *Nature* 415, 198-205 (2002); and Marban, E. supra.

There have been attempts to control the activity of certain channel proteins as a means of preventing, treating or at least reducing the severity of some heart disorders.

For instance, several synthetic $Ca^{2+}$ channel blocking drugs (also referred to as "$Ca^{2+}$ channel blockers") have been approved for use. Some $Ca^{2+}$ channel blockers are thought to impact the atrioventricular (AV) node of the heart preferentially. These agents are sometimes referred to as "AV nodal blocking" agents or like phrase. See generally Robertson, M. and D. Robertson in Goodman & Gilman's *The Pharmacological Basis of Therapeutics* 9$^{th}$ Ed. Hardman, J. G et al. Eds. (1996) Chapters 32-35, pp. 759-800 and references cited therein.

The L-type calcium channel has been reported to be a specific target for some calcium channel blockers. See Feron, O. et al. *Br J Pharmacol* 118, 659-64. (1996); and Kurita, Y. et al. *Cardiovasc Res* 54, 447-55. (2002).

However, there are reports that therapeutic use of many $Ca^{2+}$ channel blockers is associated with potentially life-threatening side-effects. These include hypotension, constipation, and heart block. See Missiaen, L. et al. *Cell Calcium* 28, 1-21 (2000); and Robertson, M., supra for a review of these and other shortcomings associated with the medical use of $Ca^{2+}$ channel blockers.

Gene therapy has been proposed as a means to prevent or treat certain heart disorders. See Marban, E. supra; Miake, J. et al. *Nature* 419: 132; Marban, E. et al. *Cold Spring Harbor*

*Symp. Quant. Biol.* Vol. LXVII: 527 (2002); and Miake, J. et al. *J. Clin. Invest.* 111: 1529 (2003); and references cited therein.

It would be desirable to have an invention that can modulate calcium channels within a pre-determined region of interest. Preferably, the invention would focally deliver a specific therapeutic composition to the region and reduce or eliminate potential for non-specific channel modulation outside that region. It would be especially desirable to have an invention that does not require use of a calcium channel blocker to modulate the calcium channel focally and within the region of interest.

SUMMARY OF THE INVENTION

The invention generally features a composition, method and system for modulating a calcium channel within a pre-determined region of interest. More particularly, the invention provides for focal delivery of a therapeutic protein that modulates the channel essentially at least near and preferably within the region. Preferred practice of the invention reduces or eliminates potential for unwanted modulation of calcium channel activity outside the region. Importantly, use of the invention does not rely on potentially harmful calcium channel blockers to modulate calcium channels focally.

We have observed that use of nearly all calcium channel blockers continues to be hindered by potentially life-threatening side-effects. We believe that most if not all of these side-effects arise from drug activity that is relatively non-specific. That is, we understand that the side-effects are often the unintended consequence of changing the activity of calcium channel proteins outside intended target areas. These and other problems continue to plague use of a wide range of calcium channel blockers.

We have also learned that cells have evolved a natural strategy for controlling calcium channel activity that employs a mammalian guanosine triphosphatase (GTPase) called Gem. It is an object of the present invention to administer the Gem protein (or a variant thereof) focally ie., to a pre-determined tissue or organ region so as to provide for specific and targeted modulation of calcium channel activity within the region. Without wishing to be bound to theory, we believe that focal delivery of the Gem protein by the invention can focally modulate calcium channel activity without significantly impacting calcium channel activity outside that region. Such targeted and specific delivery of the Gem protein (or variant) will reduce or in most cases eliminate need to employ potentially harmful calcium channel blockers. Accordingly, patient health and prognoses are expected to improve with use of the invention.

Accordingly, and in one aspect, the invention provides a method for modulating (ie. increasing or decreasing) the activity of a calcium channel protein at least near and preferably within a pre-determined tissue or organ region of a mammal. In most instances, the calcium channel will be of the L-type. In one embodiment, the method includes at least one and preferably all of the following steps:

a) contacting the region with at least one nucleic acid sequence (eg., one, two or three) encoding at least one mammalian Gem protein or variant thereof. Preferably, such contact is under conditions sufficient to express the Gem protein or variant within the region; and b) expressing the GEM protein or variant at a level sufficient to modulate the activity of the calcium channel within the region.

Practice of the foregoing method provides what is sometimes referred to herein as "genetic calcium channel blocker" activity. The phrase is intended to mean that the method harnesses the natural activity of the Gem protein in way that is genetically controllable by the user. Such activity is flexible and readily adapted to suit a particular therapeutic application. For instance, the method is generally intended to transfer genetic calcium blocker activity focally, that is, largely to the tissue or organ region in need of therapy. In most cases, significant modulation of channel proteins outside that region is substantially reduced and oftentimes avoided entirely. Importantly, focal transfer of the genetic calcium channel blocker of the invention substantially reduces or eliminates systemic sequelae that has overshadowed prior use of nearly all conventional calcium channel blockers. The invention thus provides caregivers with a rational approach for focally delivering a genetically controllable and naturally-occurring calcium channel blocker precisely where it is needed.

The nucleic acid sequence for use with the method can be administered to the mammal by one or a combination of acceptable routes. Typically, the nucleic acid is carried to the region either alone or in combination with one or more suitable microdelivery vehicles. Examples of such vehicles include, but are not limited to liposome (preferably cationic) and polymer (preferably hydrophilic) formulations and certain recombinant animal virus vectors such as those disclosed herein. The nucleic acid may be DNA, RNA including antisense DNA or RNA as well as conventional nucleic acid mimetics. In embodiments in which DNA is selected, such DNA may encode other therapeutic proteins such as hormones, enzymes, receptors or drugs of interest. Choice of a particular nucleic acid to use will be guided by recognized parameters such as desired therapeutic outcome.

Thus in one embodiment, the invention provides a method for increasing or decreasing the activity of an L-type calcium channel in which the nucleic acid encoding the Gem protein or variant is contacted with the region along with at least one of a hydrophilic polymer and cationic liposome formulation. Preferably, such contact is under conditions sufficient to express the Gem protein or variant within the region; and expressing the GEM protein or variant encoded by the nucleic acid at a level sufficient to modulate the activity of the calcium channel within the region.

However in other embodiments, it will be useful to provide the nucleic acid encoding the Gem protein or variant as part of a recombinant animal virus. In these instances, use of the virus will provide significant reliability and flexibility as it can be designed to provide relatively high or low levels of the genetic calcium channel blocker activity as required to prevent or treat medical conditions of varying severity.

For instance, a preferred recombinant animal virus for use with the invention is a an adenovirus that has been manipulated according to procedures disclosed herein. As will be apparent, the virus can be manipulated to suit population or group patients with a particular disorder. Alternatively, or in addition, the virus can be tailored more specifically for use with a particular patient or group of patients related by genetic history. In some invention embodiments, the recombinant animal virus can be adapted to provide for constitutive, partial or even complete control of the Gem protein or variant within the pre-determined tissue or organ region. Thus in embodiments in which the medical condition to be addressed by the invention is chronic and relatively severe, choice of a recombinant virus that can provide for robust and sometimes constitutive expression of the therapeutic Gem protein will be desirable. Such expression can be, for instance, for a relatively long time such as at least about a month or more up to two to three months. However in embodiments in which the medical indication is acute and perhaps much less severe or even transient, the controlled and focal expression of the Gem protein may be desirable for a much shorter time ie., less than a about a month such as a few days up to a few weeks. The ability to genetically control and focally administer the recombinant animal virus according to the invention can be achieved by one or a combination of strategies as discussed below.

The invention also provides a therapeutic method for preventing, treating, or reducing the severity of a medical condition associated with undesired calcium channel activity. In one embodiment, the method includes at least one and preferably all of the following steps:

a) contacting a pre-determined region of a tissue or organ with at least one nucleic acid (eg., one, two or three of same) such as a recombinant animal virus that includes at least one sequence encoding a Gem protein or a variant thereof, in which the contacting is under conditions sufficient to express the GEM protein or variant within the region, b) expressing the GEM protein or variant under conditions suitable to modulate the activity of the calcium channel; and c) modulating the activity of the calcium channel sufficient to prevent or treat the medical condition.

The nucleic acid encoding the Gem protein or variant can be administered to the mammal by one or a combination of acceptable routes. In particular, the nucleic acid can be carried to the region either alone or in combination with one or more suitable microdelivery vehicles as disclosed herein.

The invention method is flexible and can be used to address one or a combination of medical conditions associated with undesired calcium channel activity. Preferably, the channel is an L-type calcium channel. Broadly, such conditions are known or suspected to impact, for instance, the CNS, PNS, endocrine, or cardiovascular systems. In one particular embodiment, the method can be used to prevent or treat a range of heart conditions such as those discussed below.

In another aspect, the invention provides a therapeutic system or kit for modulating the activity of a calcium channel protein within a pre-determined tissue or organ of interest in a mammal. Preferably, the calcium channel is of the L-type. In one embodiment, the system includes at least one of and preferably all of the following as components:

(a) a nucleic acid sequence encoding at least one mammalian Gem protein or variant thereof, (b) at least one permeability agent; and optionally (c) an implementation for administering the permeability agent and nucleic acid sequence to the tissue or organ region of interest in the mammal.

In one embodiment, the nucleic acid sequence chosen is a recombinant animal virus that will typically include nucleic acid sequence that comprises as operably linked components: i) at least one sequence encoding a mammalian GEM protein or variant thereof; ii) at least one nucleic acid sequence adapted to facilitate DNA recombination; and iii) at least one nucleic acid sequence that provides an essential function of the virus.

Also provided by the invention are compositions and particularly certain recombinant animal viruses for use with the present invention.

Other uses and advantages of the invention will be apparent from following information.

BRIEF DESCRIPTION OF THE DRAWINGS

FIGS. 2A-E are graphs showing the effect of Gem on action potentials.

FIGS. 4A-G are graphs showing focal modification of AV nodal conduction by Gem gene transfer.

FIG. 6 is a table showing left ventricular function of β-Gal- and W269G-transduced mice after sham operation or TAC.

DETAILED DESCRIPTION OF THE INVENTION

Figure 1A:
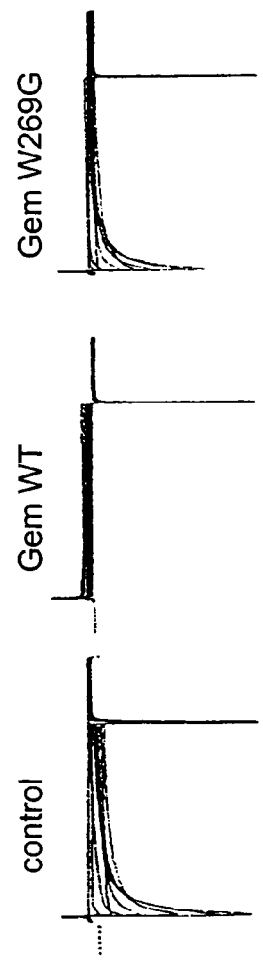
FIGS. 1A-D are graphs showing the inhibitory effect of Gem on cardiac L-type calcium currents in guinea-pig ventricular cardiomyocytes.
Figure 1B:
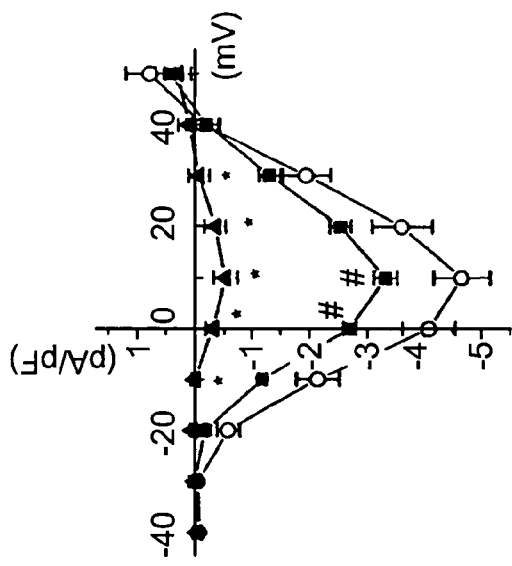

As discussed, the invention provides a composition, method and a therapeutic system or kit for increasing or decreasing activity of a calcium channel within a pre-determined tissue or organ region of a mammal. The invention has a wide spectrum of useful applications including use in the prevention or treatment of a medical condition in which abnormal calcium channel activity is known or suspected.

As also discussed, the invention provides a method that includes contacting the region of interest with at least one nucleic acid sequence that encodes at least one (preferably less than five, more preferably one, two or three of same) mammalian Gem protein or variant. When used in this context, the word "region" including plural forms means a pre-determined part of a tissue or organ that is associated with a specific biological function. Preferably, that function includes activity of a calcium channel protein, typically an L-type calcium channel. In some embodiments, the biological function is specific to that tissue or organ region while in other embodiments the function may be shared with one or more other tissues or organs.

Examples of a pre-determined organ region having L-type calcium channel activity include one or more of the four cardiac regions (great veins, atria, ventricles, and great arteries) and their connections (venoatrial, atrioventricular, and ventriculoarterial). A more preferred cardiac region is the right atrium and specifically the sinus venosus that includes the sinoatrial (SA) and atrioventricular (AV) nodes. Sometimes the SA node will be referred to herein as the heart "pacemaker" owing to its location at the sinus venosus-atrial junction. It is generally accepted that each heart beat begins in the SA node. An electrical impulse travels from the SA node and across both upper chambers, and then travels to the AV node. The impulse is thought to pass through the AV node and down to the lower chambers, causing them to contract. Each contraction of the lower chambers produces a heart beat. See generally *Gray's Anatomy* 38th Edition. Edinburgh; N.Y., Churchill Livingstone, 1995. See also published U.S. Patent Application No. 20020155101.

Other pre-determined tissue and organ regions are within the scope of the present invention. Examples include those pre-determined regions of the central (CNS) and peripheral (PNS) nervous systems known or suspected to be associated with calcium channel proteins, particularly those of the L-type. Examples of such regions include the cerebellum, hippocampus, dendate gyrus, thalamocortical region, cerebral cortex, and substantia nigra. See Sharp, A. H. et al. *Neuroscience,* 105: 599 (2001); Takada, M. et al. *Eur. J. Neurosci.* 13(4): 757 (2001); Budde, T. et al. *Eur. J. Neurosci.* 10(2):586 (1998); and Hell, J. W. et al. *J. Cell Biol.* 123(4) 949: (1993).

It will be apparent that certain regions will be associated with an accepted anatomical designation. See generally *Gray's Anatomy*, supra. Examples include but are not limited to the cerebral cortex and cerebellum in the brain and the atria and ventricles of the heart. Such anatomical regions may or may not be associated with a specific biological function.

Still other pre-determined regions in accord with the invention will include smooth muscle such as in a blood vessel and particularly arteries and veins.

More particular methods of the invention involve contacting the pre-determined region of interest with a nucleic acid sequence encoding at least one and preferably one mammalian Gem protein or variant. Suitable "contact" between the nucleic acid sequence and the target region can be accomplished by one or a combination of strategies as discussed herein including direct contact between DNA encoding the Gem protein or variant and more indirect contact such as infectious contact between a recombinant animal virus that harbors (ie. encodes) the Gem protein or variant.

General methods for delivering nucleic acid encoding an amino acid sequence have been disclosed. See eg., U.S. Pat. Nos. 5,652,225 and 5,328,470 and references cited therein. See also Vitadello, M et al. (1994) *Human Gene Therapy* 5: 11 (disclosing gene transfer in muscle); Stratford-Perricaudet, L. D. (1992) *J. Clin. Invest.* 90: 626 (providing for long-term gene transfer to mouse heart and muscles); Takeshita, S. et al. (1996) *Lab. Invest.* 74: 1061 (reporting direct gene transfer into muscle); Wolff, J. A et al. (1990) *Science* 247: 1465 (disclosing direct gene transfer into muscle in vivo); and Takeshita, S et al. (1996) *Lab. Invest.* 75: 487 (disclosing naked DNA gene transfer into blood vessels).

Thus a nucleic acid such as DNA encoding a mammalian Gem protein or variant (eg., a rodent such as a mouse or rat, rabbit or human protein) can be delivered to the pre-determined tissue or organ region of interest to modulate calcium channel function and particularly to prevent, treat or reduce the severity of a medical condition impacted by inappropriate functioning of that channel protein.

Particular polymers of interest have been disclosed in the U.S. Pat. Nos. 5,652,225 and 5,328,470, for instance and include certain hydrophilic polymers that are selected to allow incorporation of the nucleic acid to be delivered to pre-determined regions of interest such as a blood vessel and especially an arterial cell. Preferably, the hydrophilic polymer is a hydrogel polymer. Other hydrophilic polymers will work, so long as they can retain the genetic material of the present invention, so that, on contact with arterial cells, transfer of genetic material occurs. Suitable hydrogel polymers have been reported and include, but are not limited to, those selected from the group consisting of polycarboxylic acids, cellulosic polymers, gelatin, polyvinylpyrrolidone, maleic anhydride polymers, polyamides, polyvinyl alcohols, and polyethylene oxides. A particular hydrogel polymer is polyacrylic acid.

The pre-determined tissue or organ region of interest such as a blood vessel or heart tissue may be contacted with the hydrophilic polymer incorporating the DNA by nearly any acceptable means including those using an applicator such as a catheter which is coated with the DNA-bearing hydrophilic polymer. Preferably, the applicator can exert some pressure against the region of interest, to improve contact between the nucleic acid-bearing hydrophilic polymer and the arterial cells. Thus, in one embodiment a balloon catheter is preferred. Preferably, the hydrophilic polymer coats at least a portion of an inflatable balloon of the balloon catheter.

See also See U.S. Pat. Application Nos. 20020094326 and 20020155101 to Donahue, J. K et al. (disclosing other suitable catheters and related technology).

To simplify the manipulation and handling of the DNA, prior to introduction to the pre-determined region of interest, the DNA is preferably inserted into a vector, e.g., a plasmid vector such as pUC118, pBR322, or other known plasmid vectors, that includes, for example, an *E. Coli* origin of replication. See, Sambrook, et al., *Molecular Cloning: A Laboratory Manual, Cold Spring Harbor Laboratory Press,* (1989). The plasmid vector may also include a selectable marker such as the .beta.-lactamase gene for ampicillin resistance, provided that the marker polypeptide does not adversely effect the metabolism of the organism being treated. Additionally, if necessary, the DNA may be operably linked to a promoter/enhancer region capable of driving expression of the protein in the arterial cell. An example of a suitable promoter is the 763-base-pair cytomegalovirus (CMV) promoter. Normally, an enhancer is not necessary when the CMV promoter is used. The RSV and MMT promoters may also be used. Other suitable promoters are discussed below.

Suitable methods for delivering nucleic acid to the pre-determined tissue or organ region of interest have been disclosed in U.S. Pat. No. 5,652,225, for instance. Such methods generally include contacting nucleic acid to a desired microdelivery vehicle such as polymer to form a nucleic acid-polymer composition, contacting the composition to the region using suitable means such as a catheter or use of solid rods or other substrates that are often flexible to facilitate threading near and to the region of interest. Relatively inflexible substrates such as needles may be used for some applications.

In embodiments in which nucleic acid encoding the Gem protein or variant is applied directly to the tissue or organ region of interest, the precise amount of nucleic acid to add depends on the purpose of the nucleic acid and the ability of the nucleic acid to be expressed in the region of interest. Thus in embodiments in which a catheter or related implementation is used to administer naked DNA, the amount of that DNA to use will be between about 0.01 to 100 micrograms/$mm^2$, preferably about 0.1 to 50 micrograms/$mm^2$. See U.S. Pat. No. 5,652,225, for example, for more information concerning other acceptable administration strategies.

If desired, the DNA may be used with a microdelivery vehicle such as cationic liposomes. For a review of the procedures for liposome preparation, targeting and delivery of contents, see Mannino and Gould-Fogerite, *Bio Techniques,* 6:682 (1988). See also Felgner and Holm, *Bethesda Res. Lab. Focus,* 11(2):21 (1989) and Maurer, R. A., *Bethesda Res. Lab. Focus,* 11 (2):25 (1989).

See also U.S. Pat. No. 6,605,274 (disclosing gene delivery to heart); U.S. Pat. No. 6,586,410 (reporting lipid-nucleic acid compositions for gene delivery); U.S. Pat. No. 6,475,779 (reporting gene delivery polymer formulations); and U.S. Pat. No. 6,620,617, for instance.

As discussed, it will often be useful to use as a microdelivery vehicle a recombinant animal virus. In this invention embodiment, the virus will desirably include nucleic acid sequence that encodes at least one (eg., one, two, three or four copies) of a desired mammalian Gem protein (or variant) which contact is conditions that are generally sufficient to express the Gem protein, preferably within the region contacted. In embodiments in which the nucleic acid is embodied in a suitable recombinant animal virus, generally preferred conditions will be those that promote infection of the region with the virus. Examples of conditions amenable to good infection with recombinant adenovirus are discussed below. In any case, sufficient expression of the Gem protein or variant within the region modulates and preferably decreases the activity of the calcium channel protein within the region as determined by various biological and electrophysiological assays provided below. Preferably, the calcium channel treated by the method is of the L-type. A suitable Gem protein or variant is derived from a rodent (eg., rat or mouse), rabbit, or a primate such as a human.

As will become more apparent from the discussion that follows, it has been discovered that it is possible to make and use certain recombinant viruses as described herein to address a specific medical condition. This distinction is largely based on ability to essentially completely or partially block calcium channel activity, especially activity of the L-type. More specifically, it has been found that it is possible to make and use a variety of recombinant adenoviral constructs in which each has a different modulating effect on calcium channel activity, particularly of the L-type. It is thus an object of the invention to provide a panel of recombinant animal viruses made in accord with the invention in which each member of the panel can provide a specific amount of calcium channel suppression activity. Such constructs can be further adapted as needed to prevent, treat or reduce the severity of a specific medical condition.

As an illustration, it is a particular object of this invention to treat several different heart conditions that include, but are not limited to, arrhythmias, fibrillation, cardiac hypertrophy, fibrosis and cardiac remodeling. It has been found that certain recombinant animal virus as described herein and particularly those adenovirus constructs that provide robust levels of wild-type Gem protein expression, are well-suited for treating heart conditions arising from inappropriate cardiac muscle contractions eg., arrhythmias and fibrillation. However, such constructs are less suitable for treating indications involving cardiac hypertrophy, fibrosis and remodeling. Instead, it has been found that much less robust Gem activity is needed to address these disorders. Thus, it is an object of the invention to prevent, treat or reduce the severity of these and related cardiac disorders by making and using recombinant animal viruses that encode variants of the Gem protein as defined herein. Generally, such variants will provide good phosphate and guaninine binding activity but will be much less able to provide acceptable calmodulin binding. Preferred examples of such recombinant viruses and variants are provided below.

If desired, the invention can be used to provide a combined therapeutic strategy in which nucleic acid encoding the Gem protein or variant is expressed in the tissue or organ region of interest using multiple approaches. Thus in one embodiment, the recombinant animal virus encoding the Gem protein or variant is employed in the method followed by direct administration of DNA encoding the Gem protein or variant to the region using methods disclosed herein. Alternatively, such direct administration of the DNA can be used at the same time as the recombinant animal virus or at a different time such as prior to infection.

In other embodiments, it may be useful to use nucleic acid encoding two or more of the Gem proteins or variants eg., as in a nucleic acid encoding two, three, four, five or more copies of a human Gem protein or variant thereof up to about 10 of such copies. Nucleic acid encoding a full-length copy of a mammalian Gem protein and variant thereof are also envisioned.

Preferred invention methods will inhibit the L-type calcium current ($I_{Ca,L}$) by at least about 10% as determined by one or combination of suitable electrophysiological assays. See Fogoros R N. *Electrophysiologic Testing Blackwell* Science, Inc. (1999) for general disclosure relating to performing such assays.

In a particular embodiment, such methods further include inhibiting the L-type calcium channel by at least about 5%, preferably about 10%, more preferably about 20% to 50%, when compared to a suitable control as determined by what is referred to herein as a "standard electrophysiological assay". A preferred example of such as assay includes at least one and preferably all of the following steps:
1) administering a nucleic acid sequence encoding the Gem protein or variant (eg., recombinant animal virus) to a pre-determined region of the heart of a mammal under conditions that provide for a transduction efficiency of at least about 5%, preferably at least about 10%, and more preferably between from about 15% to 40% compared to a suitable control,
2) expressing the Gem protein or variant thereof within the heart at a level that represents at least about a 20% increase in protein expression compared to a control, preferably at least about a 50% increase, more preferably at least about a 100% increase with between from about 150% to 500% being generally preferred; and
3) detecting an increase or a decrease in at least one measurable electrical property of the infected heart eg., at least one of conduction, ventricular response rate, firing rate and/or pulse rate, preferably firing rate or pulse rate, relative to a baseline value. As will be appreciated, baseline values will often vary with respect to the particular recombinant animal virus selected.

Methods for determining the transduction efficiency and protein expression levels featured in the method can be roughly divided into those intended for in vivo and ex vivo applications and those intended for in vitro use (eg., with cultured primary, secondary or immortalized cells). Such methods can be used with any nucleic acid encoding a mammalian Gem protein or variant including the recombinant animal viruses disclosed herein that encode such proteins.

In embodiments in which the method is to be used for in vivo and/or ex vivo applications, electrophysiological measurements such as standard patch clamp analysis. Electrophysiology (EP) effects can be determined by measuring heart rate, conduction velocity or refractory period in vivo with EP catheters. Preferred rates of modulation are at least 1, 2, 3, 4, 5, 6, 7, 8, 9, or 10 percent difference from a baseline value. Greater increases or decreases from a baseline value also may be achieved e.g. an increase or decrease of heart rate or other measured property of at least about 12, 15, 20 or 25 percent relative to a baseline value.

In a preferred embodiment of the standard electrophysiological assay, the monitored electrical property is the QT interval in which case the assay further includes the step of shortening the QT interval (and detecting same) in the subject mammal by at least about 10%, preferably at least about 20% when compared to a suitable control. In another preferred embodiment of the assay, the monitored electrical property is at least one of the cardiac PR and AH intervals in which instance the assay further includes the step or prolonging one or both of the PR and AH intervals (and detecting same). In this embodiment, one or both of those intervals will be prolonged by at least about 10%, preferably at least about 20% when compared to a suitable control.

See Example 1 below in which over expression of the Gem protein in heart led to a substantial reduction in QT interval.

In still another preferred embodiment of the standard electrophysiological assay, the monitored electrical property in the assay is action potential duration (APD). In this example, the assay will further include the step of shortening the APD by at least about 25%, preferably at least about 40% when compared to a suitable control. Typically, the APD will be measured by reference to the $APD_{50}$ or $APD_{90}$ as a matter of convenience.

See Example 1 below showing that Gem over expression reduced the AP.

It will be appreciated that the standard electrophysiological assay is flexible and can be adapted to suit an intended use. For instance, and in one embodiment, the assay will include monitoring the QT interval alone or in combination with one or more other electrical parameters such as the APD and PR intervals. Alternatively, the APD may be monitored alone or in combination with at least one of the PR and AH intervals. Choice of a particular assay strategy will be guided by recognized parameters such as the degree of selectivity and sensitivity required.

As discussed, the foregoing general method can be used for the focal delivery of the Gem protein or variant in vivo or in some instances ex vivo. However in certain embodiments, it may be useful to monitor calcium channel protein activity by one or a combination of in vitro approaches.

For instance, in one approach, gross channel number can be assessed by measuring gating charge attributable to L-type calcium channels. The charge can be isolated and monitored specifically by comparing the signal with an L-type channel blocker such as nitrendipine. Such an assay will generally be referred to as a "standard calcium channel numbering assay" and include at least one and preferably all of the following steps:
  a) obtaining cells or tissue contacted by nucleic acid sequence encoding a mammalian Gem protein or variant such as cells or tissue infected with the recombinant animal virus expressing the Gem protein or variant thereof,
  b) contacting a portion of the cells or tissue with a suitable amount of nitrendipine as a control; and
  c) detecting the L-type calcium channel current as being indicative of the number of channel protein in the cells or tissue. Preferably, the number of L-type calcium current channels are reduced according to the assay by at least about 5%, preferably at least about 10% when compared to the control.

For instance, see Example 1 below showing that the relative numbers of L-type calcium channels was reduced by over expression of the Gem protein.

Other methods to quantify expression of the Gem protein or variant include immunological tests such as a Western blot, and recombinant DNA analysis such as quantitative PCR. Sometimes, these tests will be referred to as "standard Gem protein detection assay" or related phrase. In such embodiments, the Gem protein will be desirably over expressed by at least about 10%, preferably at least about 50%, more preferably at least about 100% up to about 300% to 1000% percent relative to a control.

See Example 2 below showing presence of endogenous Gem protein in the heart and over expression in Gem-transduced animals.

Suitable controls for measuring various parameters of the invention method will be apparent to those working in the field. Preferred controls will generally include parallel use of the same or similar nucleic acid without the encoded Gem protein or variant. In such instances, Gem encoding sequence may be replaced by an appropriate "stuffer" or linker sequence if desired. It will be appreciated that in many instances use of a control will not be needed especially when the biological activity of a particular nucleic acid is known.

As mentioned, the present invention features a method for focally modulating (preferably decreasing) the activity of a calcium channel within a pre-determined tissue or organ region of interest. Preferably, the method involves contacting the region with a nucleic acid according to the invention which in one embodiment can be recombinant animal virus that encodes the Gem protein (or variant thereof) in which the contact is under conditions sufficient to express that protein within the region. Typical methods further include expressing the Gem protein or variant at a level sufficient to modulate the activity of the L-type calcium channel within the region. In one embodiment, the method further includes administering to the mammal at least one permeability agent. That agent will sometimes be referred to herein as a "vascular" or "microvascular" permeability agent. As will be appreciated from the present disclosure and without wishing to be bound to theory, it is believed that use of the agent in accord an enhance use of the invention particularly when a recombinant adenovirus is employed to deliver the Gem protein or variant to the region of interest In particular, it is believed that use of the microvascular permeability agent can assist activity of the recombinant animal virus as used in the method.

The vascular permeability agent can be administered to the mammal before, during or after step (a) as needed to prevent, treat or reduce the severity of a particular medical indication. In one embodiment, the agent is administered before step (a). Optionally, the agent can be delivered after step (a) as well. For example, the agent can be delivered after step (a) and before step (b). Also optionally, the agent can be administered during step (a) if needed. Typically, the agent is perfused or otherwise gently administered near or directly to the predetermined region of interest. Choice of a particular perfusion rate will be guided by the particular tissue or organ for which treatment is desired. However, a typically preferred perfusion rate through a tissue or organ region of interest will be between about 0.5 ml/min to about 500 ml/min. In embodiments in which cardiac tissue is to be treated, perfusion rates of between about 1 to about 100 ml/min will often be useful.

The amount of vascular permeability agent to use will depend on recognized parameters such as the agent selected, the perfusion rate desired, etc. However for most applications, the agent will be used in an amount of about 0.01 micromoles/L to about 500 micromoles/L. Preferably, the agent will be combined with a suitable pharmaceutically acceptable vehicle prior to administration to the mammal.

One or a combination of selected vascular permeability agents can be administered to the mammal for nearly any length of time needed to provide for good contact of the recombinant animal virus with the tissue or organ region of interest. In one embodiment, the vascular permeability agent is perfused through the region for between about 10 seconds to about five or six hours. Choice of a particular perfusion time will be informed by the particular tissue or organ region for which treatment is desired. In embodiments in which cardiac tissue is to be treated, the time of perfusion can be less than about two hours, preferably between from about 30 seconds to about an hour.

One or a combination of suitable vascular permeability agents for use with the invention has been disclosed. See U.S. Pat. Application Nos. 20020094326 and 20020155101 to Donahue, J. K et al., for instance. See also Neyroud, N et al., infra.

More specifically acceptable vascular permeability agents for use with the agent include the following: substance P, histamine, acetylcholine, an adenosine nucleotide, arachidonic acid, bradykinin, endothelin, endotoxin, interleukin-2, nitroglycerin, nitric oxide, nitroprusside, a leukotriene, an oxygen radical, phospholipase, platelet activating factor, protamine, serotonin, tumor necrosis factor, vascular endothelial growth factor (VEGF) or derivative thereof, a venom, a vasoactive amine, or a nitric oxide synthase inhibitor; bradykinin, platelet-activating factor, prostaglandin $E_1$, histamine, zona occludens toxin, interleukin-2, plasma kinins. See the U.S. Patent Application Nos. 20020094326; 20020155101; and references cited therein.

It will be appreciated that in embodiments in which the vascular permeability agent is an amino acid sequence, that functional fragments of such sequences or derivatives thereof may suffice for a particular invention application. By the phrase "fragment", "function fragment" or similar term is meant a portion of an amino acid sequence (or polynucleotide encoding that sequence) that has at least about 70%, preferably at least about 80%, more preferably at least about 95% of the function of the corresponding full-length amino acid sequence (or polynucleotide encoding that sequence). Methods of detecting and quantifying functionality in such fragments are known and include the standard biological assays specific to the agent.

For instance, a preferred VEGF derivative is VEGF165. See U.S. Pat. Nos. 6,020,473 and 6,057,428, for instance.

Various vascular permeability agents including VEGF are available from a variety of sources such as Sigma-Aldrich (St. Louis, Mo.).

Additionally suitable vascular permeability agents have been disclosed in the U.S. Patent Application Nos. 20020094326 and 20020155101 and include L-N-monomethyl arginine, L-N-nitro-arginine methyl ester, and 8-Br-cGMP.

Further permeability agents suitable for use with the invention have been described in Robertson, M. and D. Robertson, supra; and include various vasodilators. Examples include but are not limited to angiotensin converting enzyme (ACE) inhibitor, angiotensin II receptor antagonist, a nitrovasodilator, phosphodiesterase inhibitor, direct vasodilator, adrenergic receptor antagonist, calcium channel blocking agent, or a sympathomimetic. A preferred vasodilator is nitroglycerin.

Still further vascular permeability agents and methods of using same have been disclosed by Neyroud, N. et al. in *Methods In Enzymol.* 346: 323 (2002). Particularly disclosed are various vascular permeability agents for use in the heart with recombinant adenoviruses. See also the U.S Patent Application Nos. 20020094326 and 20020155101.

The vascular permeability agents suitable for use with the invention will often be combined with one or more physiologically acceptable carriers such as sterile water, sterile saline, particularly isotonic saline. Other physiologically acceptable carriers are known in the field.

Another preferred vascular permeability agent for many invention embodiments is what is sometimes referred to as a "low calcium" solution. See Neyroud, N. et al. supra; and the U.S. Patent Application Nos. 20020094326 and 20020155101.

Typically, such solutions when used as a vascular permeability agent will include a solution having less than about 500 micomole/L of a calcium salt, preferably less than 100 micomole/L of the salt, with between from about 1 to about 50 micromolar being useful for many applications. Acceptable calcium salts for use with the invention will generally be chloride salts however other salts are contemplated and include inorganic and organic acid addition salts of calcium, such as sulphates, nitrates or phosphates and acetates, trifluoroacetates, propionates, succinates, benzoates, citrates, tartrates, fumarates, maleates, methane-sulfonates, isothionates, theophylline acetates, salicylates, respectively, or the like. Lower alkyl quaternary ammonium salts and the like are suitable, as well. "Pharmaceutically acceptable anions" include the group consisting of $CH_3COO^-$, $CF_3COO^-$, $Cl^-$, $SO_3^{2-}$, maleate and oleate.

A preferred combination of vascular permeability agents includes use of at least two of seratonin, VEGF (especially VEGF165), and nitroglycerin. The combination may be used alone or in combination with a low calcium solution to assist activity of the recombinant animal virus.

In embodiments in which the nucleic acid sequence encoding the Gem protein or variant is a recombinant animal virus, the amount of that virus to use with the present invention methods will vary according to understood parameters such as the medical condition to be treated, the Gem protein selected, and the specific design of the recombinant vector. However for most embodiments, use of about $10^6$ to about $10^{12}$ plaque forming units (p.f.u.) of the recombinant animal virus will be acceptable, preferably about $10^7$ to about $10^9$ p.f.u. See Neyroud, N. et al. supra for additional information in embodiments in which the virus is a recombinant adenovirus As discussed, it is an object of the present invention to reduce and preferably avoid use of conventional calcium channel blockers which in many instances have manifested undesirable side effects. However the invention is flexible and can be used alone or in combination with such blockers if treatment is indicated. In embodiments in which the invention is used with one or a combination of such drugs, the blockers can be administered to the mammal before, during or after use of the invention method. Administration of a particular calcium channel blocker in accord with the invention will be guided recognized parameters such as the general health of the mammal and the particular medical condition to be treated. However, it is contemplated that use of the invention will provide caregivers a way of substantially reducing the amount or duration of treatment associated with use of calcium channel blockers.

Examples of preferred calcium channel blockers include certain phyneylalkylamines, dihydropyridines, benzothiazepines, diphenylpipazines and diarylaminopropylamine. More particular calcium channel blockers include the following: amlodipine, bepridil, diltiazem, felodipine, isradipine, nicardipine, nifedipine, nimodipine, and verapamil. See Roberston, R. M and D. Robertson, supra, (disclosing use of various calcium channel blockers to treat cardiovascular disorders).

A preferred recombinant animal virus for use with the invention is one that has been accepted or has been used with primates and particularly human patients. Preferably, the animal virus is a recombinant adenovirus. The adenovirus genome can be readily manipulated so that it encodes and expresses a nucleic acid sequence of interest but is inactivated in terms of its ability to replicate within a host. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are known to workers in this field. See also Neyroud, N. et al., supra; Graham, F. L and Prevec, infra.

Replication-defective recombinant adenoviral vectors, can be produced in accordance with other known techniques. See, Quantin, et al., *Proc. Natl. Acad. Sci. USA,* 89:2581-2584

(1992); Stratford-Perricadet, et al., *J. Clin. Invest.*, 90:626-630 (1992); and Rosenfeld, et al., *Cell*, 68:143-155 (1992).

Although use of a recombinant adenovirus will be generally preferred for most invention applications. But in some embodiments use of an adeno-associated virus (AAV) or related virus may be helpful. Adeno-associated virus is a naturally-occurring defective virus that requires another virus, such as an adenovirus or a herpes virus, as a helper virus for efficient replication and a productive life cycle. See generally Muzyczka et al. *Curr. Topics in Micro. and Immunol.* (1992) 158:97. It is also one of the few viruses that can integrate its DNA into non-dividing cells. It has been reported to exhibit a high frequency of stable integration. See eg., Flotte et al. (1992) *Am. J. Respir. Cell. Mol. Biol.* 7:349-356; Samulski et al. (1989) *J. Virol.* 63:3822-3828; and McLaughlin et al. (1989) J. Virol. 62:1963-1973). Vectors containing as few as 300 base pairs of AAV can be packaged and can integrated.

Still other recombinant animal viruses for use with the invention include helper-dependent adenovirus, as well as chimeras of adenovirus, AAV and helper-dependent adenovirus. By "chimera" is meant a recombinant adenovirus, AAV or helper-dependent adenovirus that includes one or more components from one or more other viruses such as herpes virus, vaccinia virus, and an RNA viruses.

More particular recombinant adenoviruses for use with the invention have sequence that can be or has been manipulated by Cre or Flp recombinase. General methods for making such viruses have been disclosed. See eg., Hardy, S., et al. *J Virol* 71: 1842(1997); Hoppe, U. C. et al. *Proc Natl Acad Sci USA* 98: 5335 (2001); Johns, D. C., et al. *J Neurosci* 19, 1691 (1999); and Neyroud, N. et al., supra.

See also U.S. Pat. Nos. 6,534,314; 6,379,943 and references cited therein (disclosing materials and methods for making and using a variety of viral vectors using Cre/10x and Flp based recombination). See also U.S. Pat. No. 6,200,800; Sauer (1993), *Methods in Enzymology* 225:890; and Seibler, J., et al., (1998) *Biochemistry*, vol. 37: 6229.

See also U.S. Pat. No. 6,610,290 (disclosing certain AAV vectors for treating cardiomyopathies); U.S. Pat. No. 6,436,907 (reporting adenovirus vectors for transfering genes to muscle tissues); U.S. Pat. No. 6,610,287 (reporting herpes virus based vectors for gene therapy of the nervous system); U.S. Pat. Nos. 6,485,965; and 6,387,368 (disclosing use of certain adenovirus-AAV chimeras (hybrids) as gene delivery vehicles).

Briefly, a preferred method for making a recombinant adenovirus for use with the invention involves contacting a recombinase, preferably Cre or Flp with (a) an adenovirus acceptor vector comprising two genetically incompatible lox sequences (called L1 and L2) and (b) a donor vector comprising sequence encoding the Gem protein (or variant) flanked by the L1 and L2 sequences, or sequences which are compatible with the L1 and L2 sequences, thereby causing transfer of the Gem protein or variant thereof from the donor vector into the acceptor vector by recombination at the compatible lox sequences. Suitable acceptor and donor vectors have been reported. See eg., U.S. Pat. Nos. 6,200,800; 6,379,943; Sauer (1993), supra; and Seibler, J., et al., (1998), supra.

As used herein, the phrase "site-specific recombination," refers to DNA transfer from the donor DNA or vector to an acceptor DNA or vector. By "lox sequence" is meant a nucleotide sequence which undergoes recombination (e.g., DNA cross-over and exchange) when catalyzed by the recombinase, typically Cre, Flp or another member of the Int family of recombinases (Argos et al. (1986) *EMBO J.* 5: 433). Suitable lox sequences include, for example, the lox sequences recognized by Cre recombinase, and the frt sequences recognized by Flp recombinase. As will be appreciated, the word "recombinase" refers to any recombinase capable of catalyzing a site-specific recombination at a lox site. Suitable recombinases include, for example, Cre recombinase and Flp recombinase. See Sauer et al. (1993), supra; Buchholz et al. (1996) *Nucl. Acids Res.* 24:4256-4262; and Buchholz et al. (1998) *Nat. Biotechnol:* 16:657-662).

The method for making the recombinant animal virus for use with the invention generally utilizes a recombinase-mediated exchange reaction which takes place between identical or compatible (i.e., able to recombine with one another) lox sequences. The efficient exchange of DNA between identical or compatible lox sequences enables transfer of DNA from the donor to the acceptor vector. Significantly, once transferred from donor to acceptor vector (i.e., intermolecular transfer), the transferred DNA is stabilized or genetically "locked" into place. In addition to effective and stable DNA exchange reactions, the method is preferably used to integrate the donor sequence (ie. Gem protein or variant) into the genome of recipient cells or tissues. Successful practice of the method achieves transformation of the cells or tissues with the Gem protein or variant thereof carried by the donor.

Accordingly, a suitable recombinant animal virus for use with the invention is a recombinant adenovirus which includes nucleic acid sequence comprising as operably linked components: i) a sequence encoding the GEM protein or variant thereof; and ii) at least one nucleic acid sequence adapted to facilitate recombination using one of the foregoing recombinase systems. Preferably, the virus further includes at least one sequence that can provide an important or essential adenovirus function.

In general, suitable nucleic acid and amino acid sequences for practicing the invention can be obtained from a variety of public sources including, but not limited to, GenBank (National Center for Biotechnology Information (NCBI)), EMBL data library, SWISS-PROT (University of Geneva, Switzerland), the PIR-International database; and the American Type Culture Collection (ATCC) (10801 University Boulevard, Manassas, Va. 20110-2209). See generally Benson, D. A. et al. (1997) *Nucl. Acids. Res.* 25:1 for a description of Genbank.

More particular nucleic acids (polynucleotides) for use with the present invention are readily obtained by accessing public information from GenBank.

For example, in one approach, a desired polynucleotide sequence is obtained from GenBank. The polynucleotide itself can be made by one or a combination of routine cloning procedures including those employing PCR-based amplification and cloning techniques. For example, preparation of oligonucleotide sequence, PCR amplification of appropriate libraries, preparation of plasmid DNA, DNA cleavage with restriction enzymes, ligation of DNA, introduction of DNA into a suitable host cell, culturing the cell, and isolation and purification of the cloned polynucleotide are known techniques. See e.g., Sambrook et al. in *Molecular Cloning: A Laboratory Manual* (2d ed. 1989); and Ausubel et al. (1989), *Current Protocols in Molecular Biology*, John Wiley & Sons, New York.

The structure and function of the mammalian Gem protein and certain variants thereof have been disclosed. See Maguire, J. et al. supra; Beguin, P. et al. *Nature* 411: 701 (2001); J. S. Trimmer, supra; Fisher, R. et al. *J. Biol. Chem.* 271: 25067 (1996); and Mitsiades, L. A. et al. *Oncogene* 20(25): 3217 (2001). See also J. S. Trimmer in *Science's STKE* Jan. 8, 2002.

In particular, the nucleic acid sequence for the human and murine Gem cDNA sequences have been reported by Genbank as accession numbers O100550 and U10551, respectively. Genbank accession number NP005252 reports the following human Gem protein sequence (SEQ ID NO. 1):

```
  1  mtlnnvtmrq gtvgmqpqqq rwsipadgrh lmvqkephqy shrnrhsatp edhcrrswss 61  dstdsvisse sgntyyrvvl igeqgvgkst lanifagvhd smdsdcevlg edtyertlmv 121  dgesatiill dmwenkgene wlhdhcmqvg daylivysit drasfekase lriqlrrarq 81  tedipiilvg nksdlvrcre vsvsegraca vvfdckfiet saavqhnvke lfegivrqvr 241  lrrdskekne rrlayqkrke smprkarrfw gkivaknnkn mafklksksc hdlsvl
```
15

Sometimes the human Gem protein sequence of SEQ ID NO: 1 will be referred to herein as the "wild-type" "WT" or "normal" human Gem protein. Of course, use of other human Gem protein sequences will often be acceptable such as allelic variants of the sequence shown as SEQ ID NO: 1.

In particular, Kir/Gem is believed to suppress L-type calcium channel current by inhibiting the trafficking of its subunit to plasma membrane PC12 cells. Expression of Kir/Gem is generally low in the heart and skeletal muscle and higher in the thymus, spleen and kidney.

As used herein, the term "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

As used herein, the term "operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

As discussed, the invention methods can be used with recombinant adenoviruses that encode a mammalian Gem protein or a variant thereof. By "variant" is meant a nucleic acid sequence that encodes protein with at least about 70% sequence identify to the protein sequence shown above as SEQ ID NO. 1, preferably at least about 80%, more preferably at least about 90% or more up to about 99% identical.

As will be appreciated, to determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences. Comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444) algorithm or the algorithm of E. Meyers and W. Miller ((1989) *CABIOS,* 4:11).

Additionally suitable Gem protein variants are encoded by a nucleic acid sequence such as a cDNA which has been modified so that at least one amino acid of the protein is deleted. The deleted amino acid(s) can be contiguous or non-contiguous deletions essentially up to about 1%, more preferably about 5%, and even more preferably about 10, 20, 30, 40, up to about 50% of the length of the full-length protein sequence.

Alternatively, the cDNA encoding the Gem variant can be modified so that at least one amino acid in the encoded protein is substituted by a conservative or non-conservative amino acid. For example, a tyrosine amino acid substituted with a phenylalanine would be an example of a conservative amino acid substitution, whereas an arginine replaced with an alanine would represent a non-conservative amino acid substitution. The substituted amino acids can be contiguous or non-contiguous substitutions essentially up to about 1%, more preferably about 5%, and even more preferably about 10, 20, 30, 40, up to about 50% of the length of the full-length protein sequence.

Although generally less-preferred, the nucleic acid encoding the Gem variant can be modified so that at least one amino acid is added to the encoded protein. Preferably, an amino acid addition does not change the ORF of the cds. Typically, about 1 to 50 amino acids will be added to the encoded protein, preferably about 1 to 25 amino acids, and more preferably about 2 to 10 amino acids. Particularly preferred addition sites are at the C- or N-terminus of the selected protein.

Particular Gem variants for use with the invention feature good phosphate and guanine binding according to assays disclosed by Beguin, P et al., supra; and references cited therein. A preferred Gem variant has less than about 50% of the calmodulin binding activity of the normal Gem protein, preferably less than about 80% of such activity, with less than about 90% or more of such calmodulin activity typically being absent. Methods for determining the calmodulin activity of proteins and particularly Gem have been disclosed. For instance, one such assay involves binding to calmodulin-sepharose and detection of bound protein using standard immunological techniques. See Beguin, P et al., supra; Fisher, R. et al. *J. Biol. Chem.* 271: 25067 (1996); Moyers, J. S. et al. *J. Biol. Chem.* 272: 11832 (1997); and references cited therein.

A more specific Gem variant lacks almost all detectable calmodulin activity as determined by an suitable calmodulin binding assay. In one embodiment, the nucleic acid encoding the Gem variant features a C- or N-terminal deletion of between from about 1 to about 50 amino acids, preferably between from about 10 to about 40 amino acids. Preferably, the deletion is at the C-terminus of the protein. In another embodiment, the GEM protein variant has a single amino acid change at position 269 (W269G). See Beguin, P et al., supra, for more information about this Gem variant. See also SEQ ID NO: 1.

Another particular Gem variant for use with the invention is a naturally-occurring allelic variant of the wild-type human Gem sequence shown above as SEQ ID NO: 1.

As discussed, a preferred recombinant animal virus such as an adenovirus for use with the invention features: iii) the at least one nucleic acid sequence adapted to facilitate Cre or Flp recombination using known methods. Examples of such nucleic acid sequences include lox sequences as provided by U.S. Pat. No. 6,534,314 for instance. Preferred recombinant viruses will generally have two of such sequences. Other suitable lox sites have been reported and may be used with the invention. See U.S. Pat. No. 6,379,943 (disclosing loxP, lox511 and other sequences).

A preferred recombinant adenovirus for use with the invention methods disclosed herein includes the following nucleic acid sequences as operably linked components: i) a first inverted terminal repeat sequence (ITR), ii) a first lox P site, iii) at least one sequence encoding a mammalian GEM protein or variant thereof, preferably human wild-type Gem or variant thereof, iv) a polyadenylation signal (An), v) a second lox P site; and vi) a second inverted repeat sequence (ITR). Preferably, the virus will have one sequence encoding the desired Gem protein.

Further preferred recombinant adenoviruses for use with the invention will include as operably linked components at least one sequence that is intended to facilitate or supply an essential virus function or otherwise assist production of the encoded Gem protein sequence by providing helpful control sequences. In one embodiment, the recombinant adenovirus will further include at least one of the following sequences: viii) an adenovirus packaging site (ψ), ix) a strong viral promoter operably linked to the Gem sequence, x) internal ribosome entry site (IRES); and xi) an adenovirus early gene or functional fragment thereof eg., E2, E4 or both.

A preferred viral promoter is the 763-base-pair cytomegalovirus (CMV) promoter. The Rous sarcoma virus (RSV) (Davis, et al., *Hum Gene Ther* 4:151 (1993)) and MMT promoters may also be used. Certain proteins can be expressed using their native promoter. Other elements that can enhance expression can also be included such as an enhancer or a system that results in high levels of expression such as a tat gene and tar element. See also Neyroud, N et al. supra, for a discussion of other suitable promoter elements.

See also U.S. Published Patent Application US20020022259A1 (reporting suitable enhancer elements for facilitating gene expression in certain cardiac cells)

As used herein, the term "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

As used herein, "promoter region" is used herein in its ordinary sense to refer to a DNA regulatory sequence to which RNA polymerase binds, initiating transcription of a downstream (3' direction) coding sequence.

If desired, the recombinant animal viruses of the invention can further include at least one and preferably one detectable marker which is typically (but not exclusively) fused in frame with sequence encoding the Gem protein or variant. A preferred marker is one which provides (or can be made to provide) a colored product such as the β-Gal protein. Other suitable markers include fluorescent, phosphorescent or chemiluminescent markers such as GFP (green fluorescent protein), RFP (red fluorescent protein), luciferase, and the like.

Thus in a particular embodiment of the invention, the recombinant adenovirus for use with the method includes the following components operably linked in sequence: i) a first inverted terminal repeat sequence (ITR), ii) a first lox P site, iii) a packaging site (ψ), iv) a cytomeglovirus promoter, v) sequence encoding the GEM protein or variant, vi) an internal ribosome entry site (IRES), vii) a polyadenylation signal (An), viii) a second lox P site; ix) a sequence encoding the adenovirus early region 2 and early region 4 genes; and x) a second inverted repeat sequence (ITR). Preferably, the virus has a molecular weight between about 35 kilobases to about 40 kilobases.

Specific nucleic acid sequence for each of the operably linked components has been disclosed. For instance, see U.S. Pat. Nos. 6,379,943; 6,534,314; Hardy, S., et al. supra; Hoppe, U. C. et al. supra; Johns, D. C., et al. supra; and Neyroud, N. et al., supra.

Materials and methods for performing Cre-lox mediated recombination reactions such as with adenoviruses are available commercially. For instance, various gene cloning and expression systems for making recombinant adenoviruses that encode a desired protein are available from BD Biosciences Clontech, Palo Alto, Calif. 94303-4230 (USA).

It will be appreciated that with respect to any of the foregoing recombinant animal virus components such components may be spaced from one another by a linker sequence, provided that presence of the linker does not disrupt the function for which the virus is intended. Such linkers will generally include sequences that include restriction enzyme sites but may include other linker types as needed.

Thus in another aspect the invention provides any of the Gem-encoding recombinant adenoviruses disclosed herein including one that has the following nucleic acid sequences as operably linked components: i) a first inverted terminal repeat sequence (ITR), ii) a first lox P site, iii) at least one sequence encoding a mammalian GEM protein or variant thereof, preferably human wild-type Gem or variant thereof, iv) a polyadenylation signal (An), v) a second lox P site; and vi) a second inverted repeat sequence (ITR). Preferably, the virus will have one sequence encoding the desired Gem protein. In one embodiment, the virus further includes at least one of the following sequences: viii) an adenovirus packaging site (ψ), ix) a strong viral promoter such as the CMV promoter operably linked to the Gem sequence, x) internal ribosome entry site (IRES); and xi) an adenovirus early gene or functional fragment thereof eg., E2, E4 or both.

If desired, the recombinant adenovirus can further include at least one of the detectable sequences disclosed herein.

For some applications, it will be useful to deliver the recombinant adenovirus encoding a mammalian Gem protein (eg., wild-type human Gem) focally to the heart. In one embodiment, the focal delivery is specifically designed to transform the at least one of the atrioventricular (AV) node and sinoatrial (SA) nodes of the heart. Acceptable methods for performing the delivery have been described by Neyroud, N et al., supra. See also the published US patent application Nos. 20020094326 and 20020155101.

Briefly, a suitable recombinant adenovirus is constructed along lines discussed above. Typical perfusion protocols are generally sufficient to transfer the virus encoding the Gem protein or variant to at least about 5%, preferably at least about 10% of cardiac myocytes in the atrium. Infusion volumes of between from about 0.5 to about 500 ml are preferred. Also preferred are coronary flow rates of between from about 0.5 to about 500 ml/min. Additionally preferred perfusion protocols involve the AV nodal artery. Transformed heart cells, typically cardiac myocytes that include the polynucleotide are suitably positioned at or near the AV node.

Illustrative strategies for detecting modulation of transformed heart have been disclosed above and in Fogoros R N, supra. One strategy is to conduct a conventional electrocardiogram (ECG). Modulation of cardiac electrical properties by use of the invention is readily observed by inspection of the ECG.

The invention can be used to prevent, treat, or reduce the severity of a wide range of conditions impacted by inappropriate calcium channel activity, preferably L-type channels. Within the heart, examples include arrhythmias, fibrillation, hypertrophic cardiomyophathy, and hypertrophic obstructive cardiomyopathy, persistent sinus bradycardia, sino-atrial (S-A) block manifested as S-A Wenckebach, complete S-A block or sinus arrest (sinus impulse fails to activate the atria), and high-grade atriventricular block, cardiac related syncope, particularly Stokes-Adam syncope. Methods of the invention also will be useful to treat subjects suffering from or susceptible to bradycardia-tachycardia syndrome, and bradycardia of other causes.

Other heart conditions for which use of the invention is appropriate include particular arrhythmias such as supraventricular arrhythmias (Af, AF, etc.); ventricular arrhythmias (idiopathic VT); ischemic heart disease such as vasospastic angina; systemic hypertension; and related cardiac indications.

Administration of the nucleic acid sequence used in the methods of the invention can be in a single dose, or a series of doses separated by intervals of days, weeks or even a few months. The term "single dose" as used herein can be a solitary dose, and can also be a sustained release dose. The subject can be a mammal (e.g., a primate such as a human, chimpanzee, monkey or livestock such as cattle, goats and the like and pets such as dogs and cats) and include treatment as a pharmaceutical composition which comprises at least one recombinant animal virus or other suitable nucleic acid sequence as described herein, usually one of same. Such pharmaceutical compositions of the invention (comprising live virus in some embodiments) can be prepared and used in accordance with procedures known in the art. See eg., Neyroud, N. et al., supra; Graham, F. L and Prevec, *Methods in Mol. Biol*. The Human Press, Inc. Clifton, N.J. Vol. 7 (Gene Transfer Protocols) 109-128 (1991); ibid, 363-390.

For example, formulations containing a therapeutically effective amount of a desired recombinant animal virus or other suitable nucleic acid sequence may be presented in unit-dose or multi-dose containers, e.g., sealed ampules and vials which may require addition of the sterile liquid carrier, e.g. water injections, isotonic saline prior to use. Other compositions for perfusion applications may be helpful and include aqueous and non-aqueous sterile injection solutions which may contain anti oxidants, buffers, bacteriostat and solutes which render the formulation isotonic with the blood of the intended recipient. If desired, aqueous and non-aqueous sterile suspensions which may include suspending agents and thickening agents.

In particular, Examples 3 and 4 show that focal delivery of the Gem protein in accord with the invention achieved a reduced heart rate during fibrillation and attenuated hypertrophy.

If desired, the method can be readily adapted for other tissues and organs of interest such as those discussed herein. For instance, R. Malinow et al. have disclosed methods for directly injecting nucleic acids into the brain.

Additionally, methods of the invention can be used to provide Gem protein or variant to arteries or arterioles in a particular circulation to achieve vasodilation in that particular territory, e.g., into the arteries feeding an ischemic limb to treat Raynaud's phenomenon or intermittent claudication, or delivery into cerebral arteries to treat cerebrovascular ischemic disease, or into coronary arteries to treat angina. See references authored by D Dichek, E Nabel, D Heistad for particular methods.

As discussed, the invention further provides a therapeutic system or kit for modulating the activity of a calcium channel in a pre-determined region of a tissue or organ of a mammal. Preferably, the calcium channel is of the L-type. In one embodiment, the implementation adapted to administer the composition and the permeability agent is provided with the system as an injection needle, stent or catheter device. In a particular embodiment, the implementation is linked to a suitable pump or pumping apparatus. Preferred compositions may include a physiologically acceptable carrier such as saline. Any of the permeability agents disclosed herein may be used with the system as needed including, but not limited to VEGF165, nitroglycerin, and low calcium solutions such as those having less than about 500 μmoles/L of a calcium salt.

The present invention can be practiced alone or in combination with other methods such as involving gene therapy. See e.g, Donahue, J. et al. (1998) *Gene Therapy* 5: 630; Donahue, J. et al. *PNAS (USA)* 94: 4664 (disclosing rapid and efficient gene transfer to the heart); Akhter, S. et al. (1997) *PNAS (USA)* 94: 12100 (showing successful gene transfer to cardiac ventricular myocytes); and references cited therein.

If desired, existing cardiomyocytes may be transformed with the recombinant animal virus disclosed herein ex vivo and then implanted to the pre-determined tissue or organ region (eg., cardiac tissue) of the mammal by catheter or injection. Suitably, the existing cardiomyocytes may be harvested from the subject receiving treatment to facilitate delivery of those cells after modification (e.g. transformed with the recombinant adenovirus or other system as disclosed herein), followed by re-administration to the subject The modified cells may have been harvested from the recipient, i.e. the subject to which the cells are administered. Cardiac cells, such as sin θ-atrial node cells may be harvested from a subject such as through removal via catheter or other protocol, modified e.g. by transduction with the Gem protein or variant as disclosed herein and then administered to the subject.

Preferred subjects for treatment in accordance with the invention include domesticated animals e.g., pigs, horses, dogs, cats, sheep, goats and the like; rodents such as rats, hamsters and mice; rabbits; and primates such as monkeys, chimpanzees etc. A highly preferred mammal is a human patient, preferably a patient who has need of or suspected of having a disorder impacted by unsuitable calcium channel activity.

More specific advantages of the invention include ability to convey localized effects (by focal targeted gene delivery), reversible effects (by use of inducible vectors, including those already reported as well as new generations of such vectors, including but not limited to adeno-associated vectors using tetracycline-inducible promoters to express wild-type or variant Gem proteins), gradedness (by use of inducible vectors as noted above, in which gradedness would be achieved by titration of the dosage of the inducing agent), specificity of therapy based on the identity of the gene construct, ability to regulate therapeutic action by endogenous mechanisms (nerves or hormones) based on the identity of the viral construct, and avoidance of implantable hardware including electronic pacemakers and AICDs, along with the associated expense and morbidity.

Other advantages of the invention include the ability to focally transduce at the organ level (eg., brain, heart, vasculature) or more focally such as a pre-determined region of the organ eg., a septal artery. Preferred invention methods are much less invasive then eg., open organ surgery (of the heart, for instance) and with reference to the heart, alternative septal ablation (as with an iatrogenic infarct).

Other uses and advantages of the invention have been described in the U.S. Provisional application No. 60/415,649 and include use of the methods described herein to modulate the activity of calcium channels by gene transfer of Gem and/or Gem mutants; to alter cardiac contractile function; to alter cardiac excitability, eg., electrical conduction in the AV node; to modulate other diverse physiological processes by inhibition of L-type calcium currents, eg., excitation-coupling, excitation-secretion coupling, and memory; to couple the methods described herein with somatic gene transfer; and to use the method in combination with inducible promoters so as to achieve graded and controllable effects.

The following discussion and examples show how to make and use a focally-applicable genetic calcium channel blocker. More specifically, the Gem protein was overexpressed in the heart by somatic gene transfer. Adenovirus-mediated delivery of Gem decreased peak L-type calcium current density in ventricular myocytes, and reduced contractility. Focal delivery of Gem to the atrioventricular (AV) node reduced heart rate during atrial fibrillation, while generalized delivery of a weakly-active Gem mutant to the heart attenuated hypertrophy induced by aortic banding. As the Examples show, gene transfer of Gem functions as a genetic calcium channel blocker, the local application of which can effectively treat cardiac arrhythmia and hypertrophy without systemic sequelae. Accordingly, a recombinant adenovirus encoding Gem was transduced into the heart, resulting in the suppression of L-type calcium currents and a concomitant reduction of cardiac contractility, as expected with cardiac-specific calcium channel blockade. The Examples particularly show the utility of targeted Gem gene transfer in models of abnormal cardiac rhythm and hypertrophy.

All documents disclosed herein are incorporated by reference in their entirety.

The following non-limiting examples are illustrative of the invention.

EXAMPLE 1

Overexpression of Gem in Guinea-Pig Ventricular Cardiomyocytes

Gem overexpression was investigated so see if it could inhibit L-type calcium current ($I_{Ca,L}$) in guinea-pig ventricular cardiomyocytes. Adenoviruses were injected into the left ventricular (LV) cavity of guinea-pig hearts, and 3 days later, LV cells were isolated. Overexpression of Gem resulted in a dramatic decrease of $I_{Ca,L}$ from a peak density of 4.7±0.5 pA/pF at 10 mV (n=11) in control cells to 0.5±0.2 pA/pF at 10 mV (n=8) in Gem-transduced cells (FIG. 1a, b). The inhibitory effect of Gem on $I_{Ca,L}$ is due to the prevention of interaction between α and β subunits of L-type calcium channels by scavenging β subunits. Based on this, the effect of the less-effective W269G mutant was examined Overexpression of the W269G mutant reduced $I_{Ca,L}$ modestly, but significantly (30% inhibition vs. control, 3.3±0.2 pA/pF at 10 mV, n=10), consistent with translocation of mutant Gem to the nucleus from the usual cytosolic distribution of Gem. See Beguin, P. et al. supra.

FIGS. 1A-D are explained in more detail as follows.

FIGS. 1A-D show the inhibitory effect of Gem on cardiac L-type calcium currents in guinea-pig ventricular cardiomyocytes. (FIG. 1A), Representative L-type calcium currents in a control, a wild type Gem-transduced cell, and a W269G mutant-transduced cell. (FIG. 1B), The current-voltage relationships of L-type calcium currents in control, wild type Gem-transduced, and W269G mutant-transduced cells. L-type calcium current densities are significantly reduced in wild type Gem-transduced cells (▲, n=8), compared with control cells (○, n=11), whereas W269G mutant had a slight effect (■, n=10). (FIG. 1C), Representative recordings of calcium channel gating current in a control, wild type Gem-transduced, and W269G mutant-transduced cell. (FIG. 1D), Pooled data for calcium channel gating charge in control, wild type Gem-transduced, and W269G mutant-transduced cells. The Q versus V data were fit to a Boltzmann distribution using the following equation: $Q=Q_{max}/[1+\exp((V-V_{1/2})/k]$, where $V_{1/2}$ is the half maximum potential, k is the slope factor. Calcium channel gating charge was significantly reduced in wild type Gem-transduced cells compared with control cells, whereas restored in W269G mutant-transduced cells.

Figure 1C:
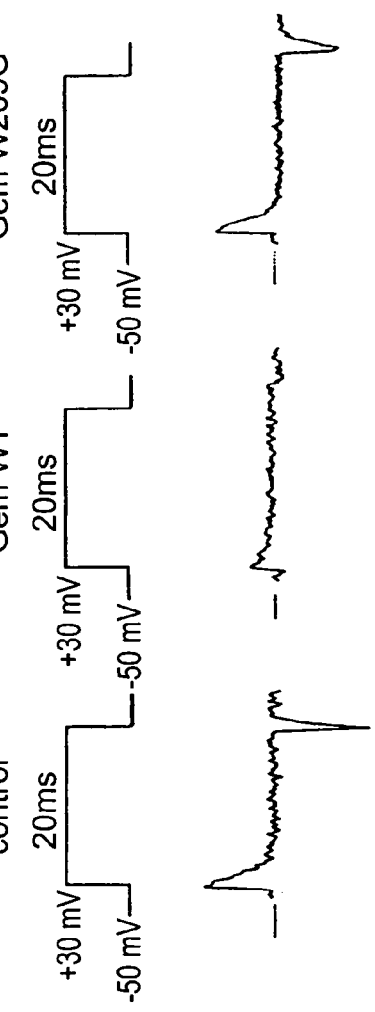
Figure 1D:
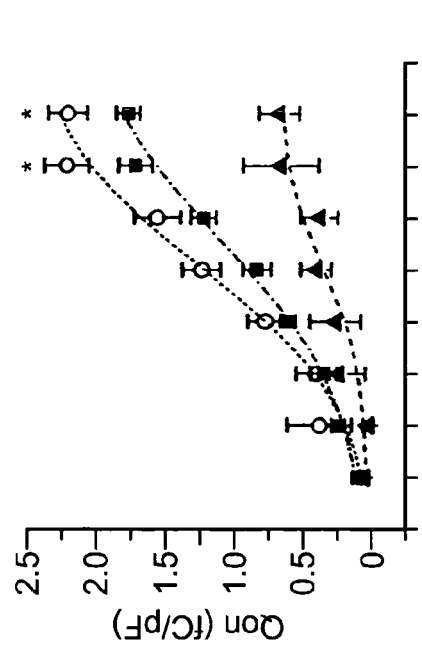

Next, the mechanism of $I_{Ca,L}$ suppression by Gem overexpression was examined. a It was believed that a decrease in the number of functional channels would be predicted. This is consistent with the observation that Gem binds to β subunits of calcium channels and inhibits the trafficking of a subunits to the plasma membrane. See Beguin, P. et al., supra. To assess channel number, the gating charge attributable to L-type calcium channels was measured and we isolated the calcium-channel-specific component using 10 μmol/L nitrendipine, an L-type channel blocker. See Bolger, G. T. et al. *Biochem Biophys Res Commun* 104, 1604-9. (1982); and Bean, B. P. *Proc Natl Acad Sci USA* 81, 6388-92. (1984). Overexpression of Gem resulted in a marked reduction of nitrendipine-sensitive gating currents compared with control (FIG. 1c, d). The gating currents during depolarization were integrated to calculate charge movements during depolarization ($Q_{on}$). Control $Q_{on}$ was significantly greater than that in Gem-transduced myocytes (2.2±0.2 fC/pF at +30 mV, n=6 vs. 0.67±0.1 fC/pF at +30 mV, n=6, P=0.001). The voltage dependence of $Q_{on}$ was comparable in control and Gem-transduced cells, as demonstrated by simultaneously-fit Boltzmann distributions to the mean data sets, with $V_{1/2}$=0.5 mV, k=13.3 mV in control and $V_{1/2}$=−0.3 mV, k=9.8 mV in Gem-transduced cells. W269G mutant only modestly affected these parameters (1.8±0.1 fC/pF at +30 mV, $V_{1/2}$=5.5 mV, k=15.5 mV, n=6). These results indicate that the number of functional calcium channels in the cell membrane is indeed decreased in Gem-transduced cells, compared with control cells. Those channels that do make it to the surface, however, appear to have normal gating properties.

The effects of Gem overexpression on action potentials in ventricular cardiomyocytes was examined. Overexpression of Gem resulted in the abbreviation of action potential duration (APD) without any change in resting membrane potential (−84.6±0.4 mV vs. −84.9±0.4 mV) or phase 1 depolarization (FIGS. 2A-C). Both $APD_{50}$ and $APD_{90}$ were significantly shortened in Gem-transduced cells compared with control cells, whereas overexpression of W269G mutant had little effect (FIGS. 2A-D). Notably, the robust plateau phase was blunted in Gem-transduced myocytes. The modification of action potentials became more pronounced as $I_{Ca,L}$ decreased. There was a clear correlation between $I_{Ca,L}$ density, calculated as the nitrendipine-sensitive ionic current, and $APD_{90}$; both were reduced in Gem-transduced myocytes compared with control cells (n=21, r=0.87, P<0.0001) (FIG. 2E).

FIGS. 2A-E are explained in more detail as follows.

FIGS. 2A-E show the effect of Gem on action potentials. (FIGS. 2A-C), Representative action potentials in a control (FIG. 2A), a wild type Gem-transduced cell (FIG. 2B), and a W269G mutant-transduced cell (FIG. 2C). Action potentials in wild type Gem-transduced cells were abbreviated and lacked a robust plateau phase. (FIG. 2D), Pooled data for action potential duration in control, Gem-transduced cells, and W269G mutant-transduced cells. Action potential duration was significantly reduced in wild type Gem-transduced cells (n=12), compared with control cells (n=12), whereas restored in W269G mutant-transduced cells. (FIG. 2E), A highly significant correlation between $APD_{90}$ and L-type calcium current density (r=0.866, P<0.0001). ■, control (nitrendipine −), ○, wild type Gem-transduced, ▲, control (nitrendipine +).

EXAMPLE 2

In Vivo Phenotype of Cardiac Calcium Channel Blockade

Figure 3A:
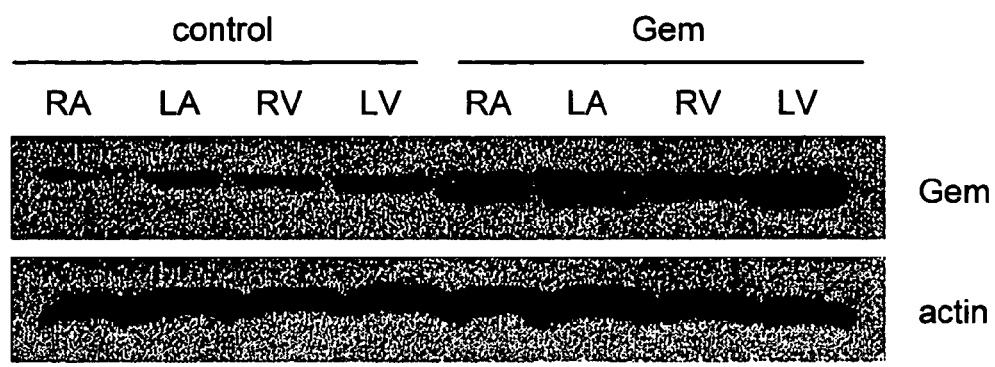
FIGS. 3A is a representation of a gel and FIGS. 3B-E are graphs showing the in vivo phenotype of cardiac calcium channel blockade by Gem transduction into guinea pig hearts.

There has been a report that the LV cavity injection method resulted in a transduction efficiency of 15-25% in the heart. See Miake, J. et al. *J Clin Invest* 111, 1529-36 (2003). Western blot analysis (FIG. 3) confirmed Gem overexpression in all cardiac chambers, amounting to a 300±60% increase in the Gem-transduced animals relative to control levels (P=0.002). The presence of endogenous Gem in heart was observed.

To assess the electrophysiological phenotype in intact animals, electrocardiograms were performed 3-4 days after injection of adenoviruses into the LV cavity. The QT interval was shortened in Gem-transduced animals compared with control animals (e.g., FIG. 3, b). See Bean, B. P. *Proc Nat Acad Sci USA* 81, 6388-92 (1984). Consistent with action potential recordings in isolated Gem-transduced myocytes, the QTc intervals of the EKG measured 3 days after transduction were abbreviated in Gem-transduced animals compared with the same animals immediately after surgery (165±3.5 ms vs. 148±2.3 ms, n=9, P<0.05). In contrast, no change in the QTc interval was observed in the animals transduced with only GFP (165±3.3 ms vs. 166±1.8 ms, n=6) or W269G mutant (166±1.8 ms vs. 163±1.1 ms, n=7). Interestingly, we observed PQ interval prolongation in one of the Gem-transduced animals (central panel, FIG. 3, b), which was presumably induced by especially intense expression of Gem in the AV node. In the next section, the AV node was targeted in a model of cardiac arrhythmia.

FIGS. 3A-E are explained in more detail as follows.

Figures 3B, 3C, 3D:
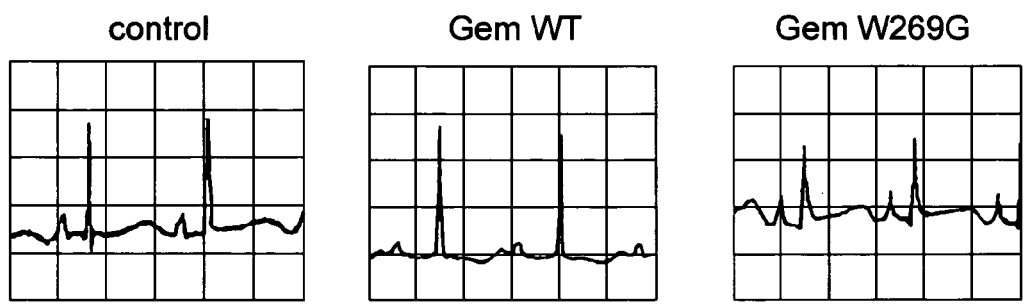
Figure 3E:
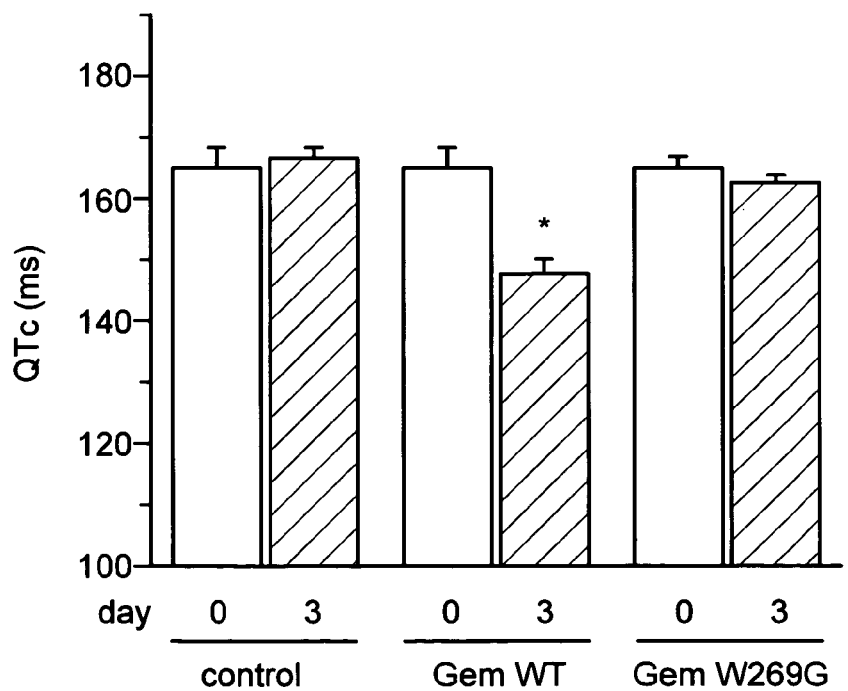

FIGS. 3A-E show the in vivo phenotype of cardiac calcium channel blockade by Gem transduction into guinea pig hearts. (FIG. 3A), Western blot of heart tissue in each region (RA, LA, RV, LV) demonstrates Gem overexpression in the AdCIG-Gem transduced animals. (FIGS. 3B-D), EKG traces from a control (FIG. 3B), a Gem WT-transduced (FIG. 3C), and W269G mutant-transduced animal (FIG. 3D). The QT interval was shortened, and the PQ interval was prolonged in a Gem WT-transduced animal, compared with a control animal as well as a W269G mutant-transduced animal. (FIG. 3E), Pooled data for QTc interval calculated by a square root method. QTc interval was significantly shortened 3 days after gene delivery compared with that immediately after surgery in wild type Gem-transduced animals, whereas there was no change in control as well as W269G mutant-transduced animals.

EXAMPLE 3

Focal Modification of AV Nodal Conduction by Gem Gene Transfer

Atrial fibrillation is a disturbance of cardiac rhythm in which a rapid heart rate produces breathlessness and decreased exercise tolerance. Inhibition of AV nodal conduction, by calcium channel blockade, is the mainstay of drug therapy, but such therapy is fraught with side effects due to calcium channel blockade outside the AV node.

An intracoronary perfusion model for adenoviral gene delivery in pigs has been reported. It succeeded in the modification of AV nodal conduction by overexpression of the inhibitory G protein, Gαi2. See Donahue, J. K. et al. *Nat Med* 6, 1395-8. (2000). Overexpression of Gem in the AV node would likewise slow AV nodal conduction, with benefit for rate control in atrial fibrillation. Seven days after gene transfer in the same pig model, Gem-transduced animals revealed prolongation of the PR interval on the surface EKG, and the AH interval (but not the HV interval) on the intracardiac electrogram, confirming slowed conduction in the AV node (FIG. 4, c-e). During acute episodes of atrial fibrillation (FIG. 4, a), overexpression of Gem in the AV node caused a 20% reduction in the ventricular rate during atrial fibrillation (FIG. 4, f). This effect persisted in the setting of β-adrenergic stimulation as well as cholinergic inhibition (FIG. 4, g). Thus, focal calcium channel blockade induced by Gem gene transfer into the AV node effectively reduces the heart rate in atrial fibrillation.

FIGS. 4A-G are explained in more detail as follows.

FIGS. 4A-G show focal modification of AV nodal conduction by Gem gene transfer. (FIG. 4A) Representative EKG recordings during sinus rhythm and atrial fibrillation before gene transfer of Gem. Scale bar=200 ms. (FIG. 4B) Representative EKG recordings during sinus rhythm and atrial fibrillation 7 days after gene transfer of Gem. Scale bar=200 ms. (FIG. 4C) PR interval on the surface EKG before (day 0) and 7 days after transduction (day 7). *, p<0.05 vs. PR interval at day 0 (n=4). (FIG. 4D) AH interval on the intracardiac electrogram before (day 0) and 7 days after transduction (day 7). *, p<0.05 vs. AH interval at day 0 (n=4). (FIG. 4E) HV interval on the intracardiac electrogram before (day 0) and 7 days after transduction (day 7). (FIG. 4F) Heart rate during sinus rhythm and atrial fibrillation before (day 0) and 7 days after transduction (day 7). *, p<0.05 vs. heart rate at day 0 (n=4). (FIG. 4G) Heart rate during atrial fibrillation stimulated by isoproterenol (ISP) or atropine before (day 0) and 7 days after transduction (day 7). *, p<0.05 vs. heart rate at day 0 (n=4).

EXAMPLE 4

Attenuation of Cardiac Hypertrophy by Gem Overexpression

Excessive overgrowth of the heart leads to abnormal ventricular function and lethal arrhythmias. Calcium influx through L-type calcium channels influences myocyte hypertrophy in vitro. See e.g, Lubic, S. P. et al. *J Mol Cell Cardiol* 27, 917-25 (1995)), rationalizing the efficacy of calcium channel blockers to induce regression of hypertrophy in several clinical studies. See also Arita, M. et al. *Jpn Circ J* 54, 575-80 (1990); and Smith, V. E. et al. *J Am Coll Cardiol* 8, 1449-54 (1986).

It has been reported that chronic blockade of L-type $Ca^{2+}$ channels suppresses the activation of calcineurin and the development of cardiac hypertrophy in spontaneously hypertensive rats. See Zou, Y. et al. *Hypertens Res* 25, 117-24. (2002). Nevertheless, the ability of calcium channel blockers to suppress cardiac hypertrophy by direct effects on the heart is being investigated. See Manolis, A. J. et al. *Am J Hypertens* 11, 640-8 (1998); and Ito, H. et al. *Circ Res* 69, 209-15 (1991)). As discussed, many calcium channel blockers have effects elsewhere in the body (e.g., to lower blood pressure). In order to address the issue, widespread, heart-specific overexpression of Gem using an adenovirus-mediated in vivo gene delivery system which results in 60% transduction efficiency in mice was achieved. It was found that transduction of wild-type Gem into the heart killed some mice. That result was predicted if transduction effeciency was too high and if calcium influx were strongly blocked in the majority of heart cells. Therefore, the W269G mutant, whose calcium channel blockade is much less intense than Gem WT was used instead.

Figure 5A:
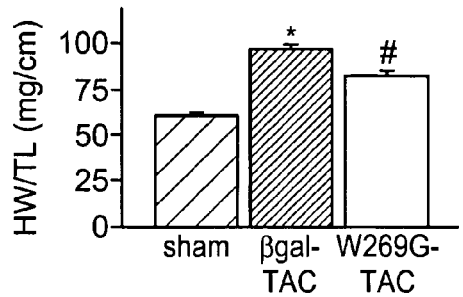
FIGS. 5A-F, H are graphs and FIG. 5G provides photographs showing attenuation of cardiac hypertrophy progression by W269G mutant over expression.
Figure 5B:
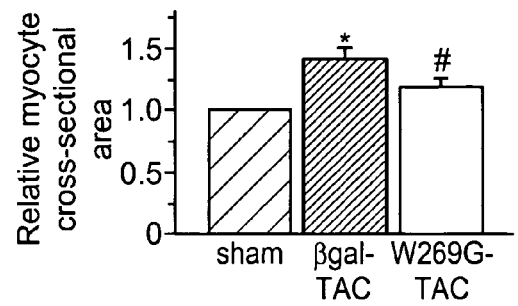
Figure 5C:
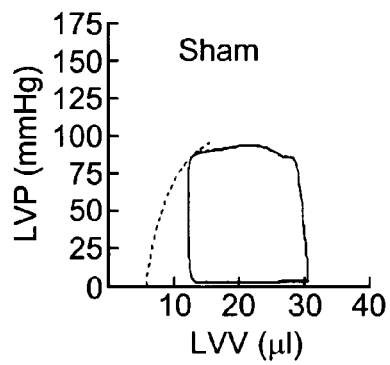
Figure 5D:
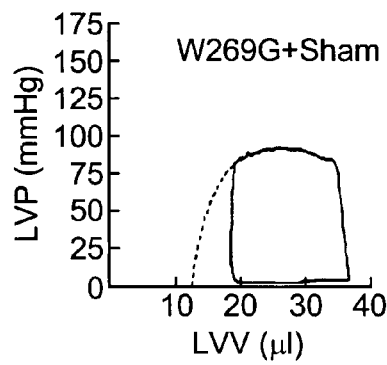
Figure 5E:
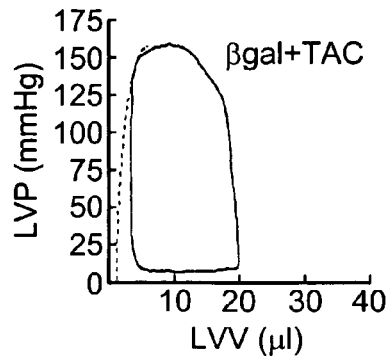
Figure 5F:
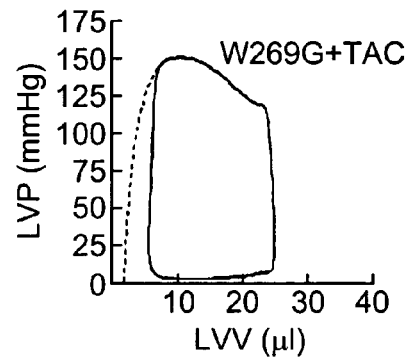

To test whether W269G expression could attenuate pressure-overload-induced cardiac hypertrophy, we surgically constricted the thoracic aorta (TAC) in mice that had received either W269G or β-galactosidase, with sham-operated controls for both interventions. Seven days after TAC, hypertrophy was evident in the β-gal-TAC group compared with sham group, as assessed by the increased ratio between heart weight and tibial length (HW/TL). Interestingly, overexpression of W269G attenuated the increase in HW/TL as compared with the β-gal-TAC group (FIG. 5A). To examine whether W269G changes heart size through the regulation of myocyte cell size, the myocyte cross-sectional area of the LV myocardium was measured in hearts from mice subjected to aortic banding for 1 week. Reinforcing the heart weight data, histological analysis revealed an increase of cardiac myocyte cross-sectional area with TAC, which was substantially attenuated in W269G-TAC as compared with β-gal-TAC (FIG. 5B).

Left-ventricular pressure-volume measurements showed the characteristic functional abnormalities of cardiac hypertrophy with enhanced systolic function and decreased LV volume, these changes were more severe in β-gal-TAC than in sham (FIGS. 5C-F). Expression of mutant Gem decreased various indices of systolic function relative to the β-gal-TAC controls, while there was no significant difference in diastolic function between these two groups (FIG. 6).

Figure 5G:
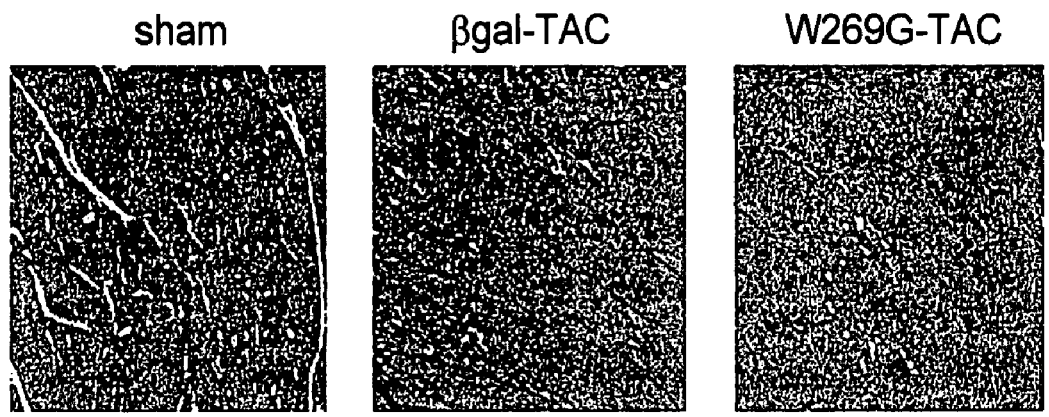
Figure 5H:
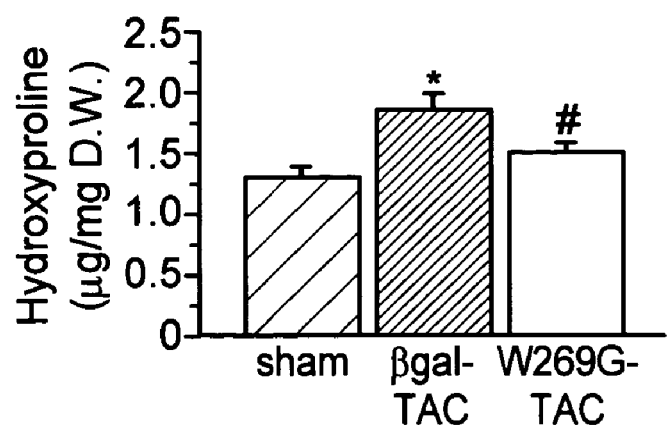

We additionally assessed whether W269G attenuates the development of cardiac fibrosis, a key pathological process which predisposes the hypertrophied heart to arrhythmias. Histological stains for collagen revealed extensive fibrosis in the β-gal-TAC group (but not the sham group). The extent of such fibrosis was much-reduced in W269G-TAC compared with β-gal-TAC (FIG. 5G); likewise, hydroxyproline incorporation, which assays collagen deposition, was decreased (FIG. 5H). Collectively, the data reveal that cardiac-specific expression of W269G attenuates myocyte and organ hypertrophy, ameliorates ventricular function and suppresses fibrosis during pathological pressure overload.

FIGS. 5A-H are explained in more detail as follows.

FIGS. 5A-G show attenuation of cardiac hypertrophy progression by W269G mutant overexpression. (FIG. 5A) HW/TL 7 days after sham (n=10), βgal-TAC (n=7), and W269G-TAC operation (n=7). (FIG. 5B) Myocyte cross-sectional area measurements in sham, βgal-TAC, and W269G-TAC operated hearts (n=4 hearts per group). (FIGS. 5C-F) Pressure-volume loops from representative WT-sham operated, βgal-Tac, W269G-sham, W269G mutant-TAC mice. (FIG. 5G) Representative trichrome-stained sections from a sham operated, βgal-TAC, and W269G mutant-TAC heart. (FIG. 5H) Pooled data for hydroxyproline in a sham operated, βgal-TAC, and W269G mutant-TAC group (n=5 hearts per group). *, p<0.01 vs sham group, #, p<0.05 vs βgal-TAC group.

The following materials and methods were used as needed to perform manipulations outlined in the Examples.

A. Plasmid Construction and Adenovirus Preparation

The full-length coding sequence of Gem was cloned into the multiple cloning site of adenovirus shuttle vector pAdCIG to generate pAdCIG-Gem. This construct is a bicistronic constructs (through an internal ribosome entry site) driven by a cytomegalovirus promoter and carrying green fluorescent protein (GFP) as a reporter. The point mutation W269G was introduced into Gem by site-directed mutagenesis, creating the vector pAdCIG-Gem W269G. Detailed methods of adenovirus vector construction have been described. See Hardy, S. et al. *J Virol* 71, 1842-9. (1997); Hoppe, U. C. et al. *Proc Natl Acad Sci USA* 98,5335-40; and (2001). Johns, D. C. et al. *J Neurosci* 19, 1691-7. (1999).

Figures 7, 8:
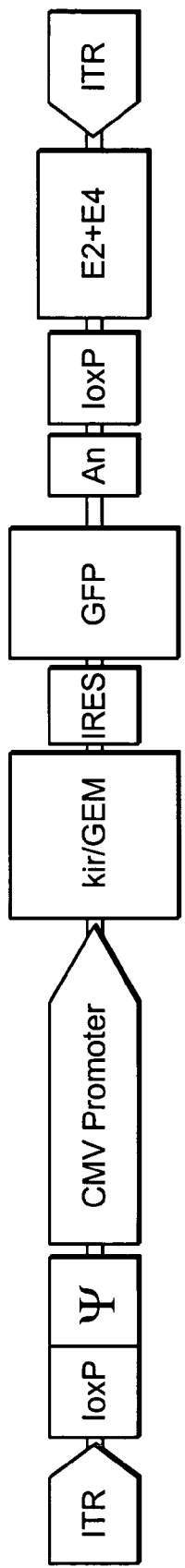
FIG. 7 is a drawing showing a particular recombinant adenovirus construct of the invention.
FIG. 8 is a table showing a comparison of ECG parameters at 72 hours after gene delivery in control and kir/gem-transduced animals.

The structure of the construct is shown schematically in FIG. 7.

In vivo adenoviral transduction into guinea pig hearts was performed as described. See Mazhari, R. et al. *J Clin Invest* 109, 1083-90. (2002). Adenoviruses (160 μl, equivalent to about $3\times10^9$ plaque forming units (p.f.u.)) were injected in the LV cavity of guinea pigs (280-340 g), while the aorta and pulmonary artery were clamped for 50-60 seconds.

B. Myocyte Isolation and Electrophysiology

Seventy-two hours after gene delivery, myocytes were isolated from the left ventricles of guinea pigs by enzymatic digestion. See Hoppe, U. C. et al. *Proc Natl Acad Sci USA* 98, 5335-40. (2001). Membrane currents and action potentials were recorded using whole-cell patch clamp technique at 37° C. Uncompensated capacitance currents in response to small hyperpolarizing voltage steps were recorded for off-line integration as a means of assaying cell surface area. Action potentials were initiated by short depolarizing current pulses (2 ms, 100-300 pA, 10-15% over the threshold) applied every 3 s. Transduced cells were recognized by their obvious green fluorescence.

To measure gating currents, ionic currents were blocked by 2 mmol/L $CdCl_2$ and 0.1 mmol/L $LaCl_3$. See Colecraft, H. M. et al. *J Physiol* 541, 435-52 (2002). Leaks and capacitative transients were subtracted by a P/−4 protocol from a −100 mV holding potential. Charge movement (Q) was quantified by calculating the area under the curve for each trace, using steady-state level of the current as a baseline.

A table showing a comparison of ECG parameters at 72 hours after gene delivery in control and kir/gem-transduced animals is shown in FIG. 8.

C. Hemodynamic Analysis

Mice (7 days post-transfection or sham) were anesthetized, intubated and ventilated, and studied by pressure-volume catheterization. See Georgakopoulos, D. et al. *J Physiol* 534, 535-45 (2001). A 1.8F catheter (SPR-719, Millar, Tex.) was advanced via the LV apex to lie along the longitudinal axis, and connected to a stimulation/analysis system to yield pressure-volume loops. To assess heart-rate modulation of cardiac function, a 2F pacing catheter (NuMed, Nicholville, N.Y.) was placed in the esophagus to achieve atrial pacing. See Arita, M. et al. *Jpn Circ J* 54, 575-80 (1990). Spontaneous sinus rate was first slowed using the $I_f$ inhibitor ULFS-49 (Boehringer Ingelheim; 15-20 mg kg$^{-1}$, I.P.). See Georgakopoulos, D. et al. *J Physiol* 534, 535-45 (2001).

Figure 9A:
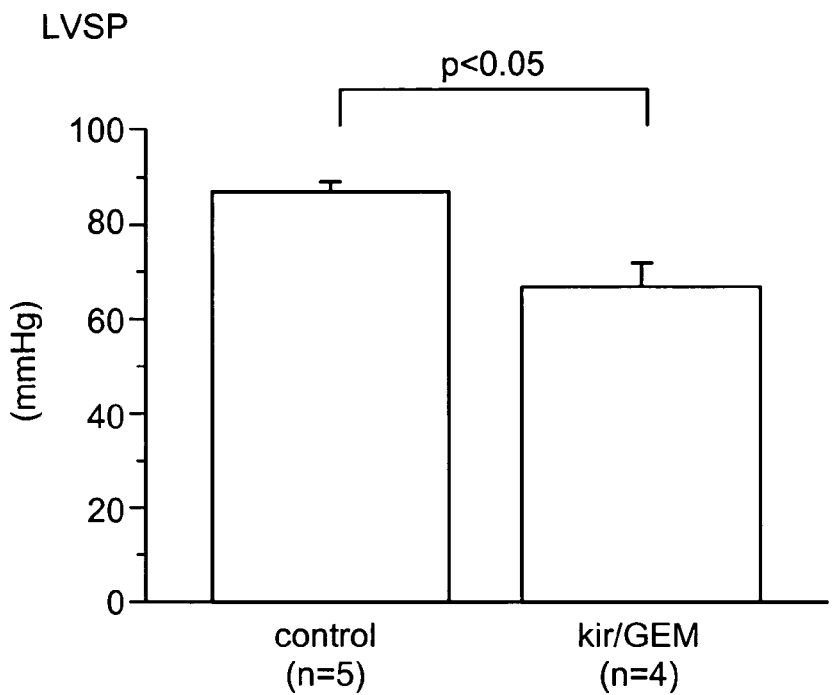
FIGS. 9A-B are graphs summarizing effects of kir/gem on hemodynamics.
Figure 9B:
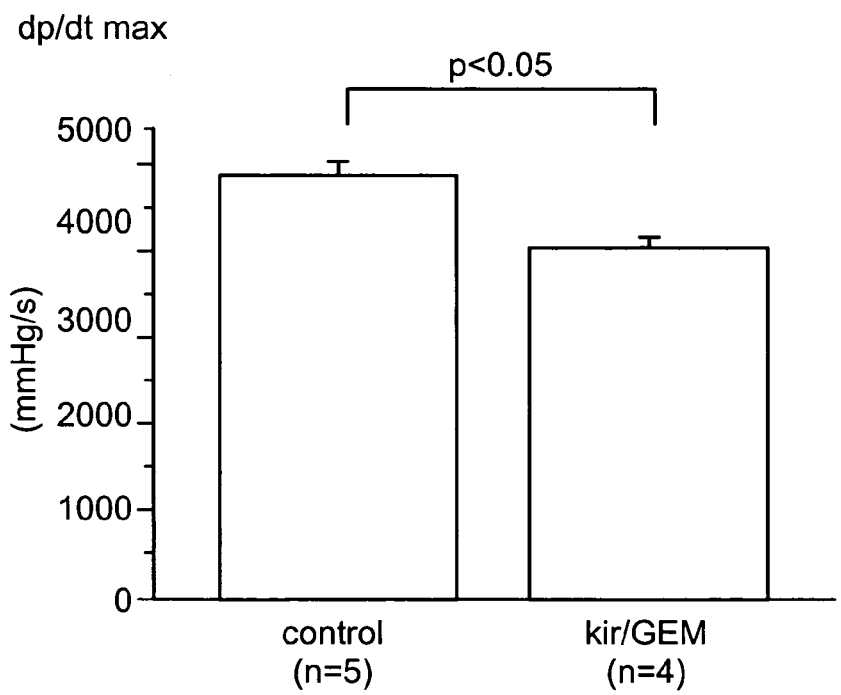

FIGS. 9A-B show graphs summarizing effects of kir/gem on hemodynamics.

D. Focal Gene Transfer into AV Node

Adenoviral gene transfer into AV node was performed as described. See Donahue, J. K. et al. *Nat Med* 6, 1395-8. (2000).

Briefly, immediately before catheterization, domestic swine (25-30 kg) received 25 mg sildenafil orally. The right carotid artery, right internal jugular vein and right femoral vein were accessed by sterile surgical technique, and introducer sheaths were inserted into each vessel. After baseline EP study, the right coronary artery was catheterized via the right femoral artery. The AV nodal branch was selected with a 0.014-inch guide wire, over which a 2.7 F infusion catheter was inserted into the AV nodal artery. The following solutions were infused through the catheter: 10 ml normal saline (NS) containing 5 µg VEGF165 and 200 µg nitroglycerin over 3 minutes, 1 ml NS containing $1.0 \times 10^{10}$ p.f.u. adenovirus and 20 µg nitroglycerin over 30 s, and 2.0 ml NS over 30 s.

E. Mouse Hypertrophy Experiments

Gene transfer of an adenovirus into mice hearts was performed as follows. Briefly, topical 2% lidocaine gel was applied to the chest, and the thorax was accessed by right lateral incision approximately 0.5 cm above the diaphragm. The anesthetized mouse was then cooled with a water jacket to a core temperature of 18-21° C. The aorta was clamped distal to the takeoff of the left subclavian artery. Both descending aorta and inferior vena cava were cross-clamped for 9 min duration and virus ($1 \times 10^9$ p.f.u./ml) injected into the right internal jugular vein with 20 microliters lipofectamine and 1 microgram/kg histamine. After releasing the aortic clamp, isoproterenol (3-10 ng/kg/min i.v.) and/or transesophageal pacing (NuMed, Hopkinton, N.Y.,) (Georgakopoulos, D. et al. *J Physiol* 534, 535-45 (2001)), were used for cardiac support if needed, and mice warmed to 37° C. over 30-40 min. The chest was closed, and animals extubated. Subsequent analysis was made 3 days after transfection. Following transfection, the mouse was placed in the supine position and the transverse aorta was isolated by entering the extrapleural space above the first rib. A 7-0 nylon suture ligature was tied around the transverse aorta against a 27-gauge needle to produce a 65-70% contriction.

F. Statistical Analysis

All the data shown are mean±SEM. Statistical differences were determined using repeated measures ANOVA and Student's paired t-test, where appropriate, and $P<0.05$ was considered to indicate statistical significance.

The foregoing discussion and examples show how to make and use a genetic calcium channel blocker in the heart. In particular, overexpression of Gem WT prominently inhibited $I_{Ca,L}$ in guinea-pig ventricular cardiomyocytes, resulting in marked abbreviation of APD, while W269G mutant had only weak effects. Furthermore, in vivo delivery of Gem WT shortened the QT interval, consistent with the abbreviation of APD seen in isolated cardiomyocytes. Taking advantage of the distinct difference in potency between Gem WT and Gem mutant, one or the other gene was transferred depending on the targeted pathological condition. The prominent inhibitory effect of Gem WT on $I_{Ca,L}$ was effective in genetic modification of AV nodal conduction to treat atrial fibrillation, a common arrhythmia which afflicts over 2 million Americans. Once AF becomes chronic, therapy is directed at achieving rate control with the use of AV nodal blocking agents. Wyse, D. G. et al. *N Engl J Med* 347, 1825-33. (2002). Since $I_{Ca,L}$ underlies impulse conduction in the AV node, calcium channel blockers are preferred agents for rate control during AF, but often are not tolerated due to contractile depression from block of non-AV nodal calcium channels in the heart, or hypotension from block of non-cardiac channels. As shown in the Examples, the inventors achieved focal modification of AV nodal conduction by gene transfer of Gem WT via the AV nodal artery; the resultant regionally-selective $I_{Ca,L}$ blockade is effective at rate control during AF, without undermining calcium channel function in the pumping chambers of the heart.

This disclosure also shows that the invention can be used to prevent cardiac remodeling and hypertrophy by transduction of a particular Gem variant ie., the mutant Gem described in the Examples. Changes in intracellular $Ca^{2+}$ have long been associated with the onset and progression of cardiac hypertrophy and associated cardiomyopathies. Heart-specific expression of the Gem mutant attenuated cardiac hypertrophy without reducing afterload, implying the Gem mutant had a direct effect on cardiac hypertrophy in vivo. Furthermore, in vitro experiments using neonatal rat cardiomyocytes revealed that overexpression of Gem abrogated the progression of hypertrophy induced by phenylephrine.

The disclosure further shows that the invention can be used to modulate cardiac contractility. Hemodynamic studies showed that there was a slight trend of negative inotropy in mutant Gem-transduced hearts compared with sham operated-hearts in mice (FIG. 6). In addition, overexpression of Gem WT in guinea pig hearts resulted in the significant negative inotropic effect, indicating that gene transfer of Gem (WT or mutant) is useful to reduce cardiac contractility. Negative inotropic drugs are first-line treatment for patients with hypertrophic obstructive cardiomyopathy (HOCM) (Spirito, P. et al. *N Engl J Med* 336, 775-85 (1997)), to reduce contractile activity in the hypertrophic heart as a means of improving overall pumping efficacy. In accordance with this idea, iatrogenic myocardial infarction has been developed as a means of treating severe HOCM. Nielsen, C. D. et al. *Cardiol Rev* 10, 108-18 (2002). Sigwart, U. *Lancet* 346, 211-4 (1995). Chang, S. M. et al. *J Am Coll Cardiol* 42, 296-300 (2003). However, the utility of this radically destructive therapy may be limited in some settings. The present invention provides an attractive alternative approach, in that the myocardium is rendered regionally passive while remaining alive and excitable.

While the invention has been described with reference to specific methods and embodiments, it will be appreciated that various modifications and changes may be made without departing from the invention. All documents disclosed herein are incorporated by reference.

What is claimed is:

1. A method for blocking activity of a calcium channel in a predetermined region of excitable cardiac cells in a mammal, the method comprising:
contacting directly the excitable cardiac cells with a recombinant adenovirus comprising a nucleic acid encoding a GEM protein having the amino acid sequence according to SEQ ID NO: 1, under conditions sufficient for the excitable cardiac cells to express the GEM protein,
wherein the GEM protein is expressed at a level sufficient to partially block activity of the calcium channel, and
wherein partially blocking the activity of the calcium channel results in a shortening of a cardiac QT interval and/or a reduction of heart rate in atrial fibrillation.

2. The method of claim 1, wherein the region of excitable cardiac cells is associated with a specific biological function.

3. The method of claim 1 or 2, wherein the region of excitable cardiac cells has a specific anatomical designation.

4. The method of claim 1, wherein the method further comprises inhibiting L-type calcium current (ICa,L) by at least 10% as determined by a standard electrophysiological assay.

5. The method of claim 1, wherein the nucleic acid is a DNA molecule.

6. The method of claim 1, wherein blocking of the activity of the calcium channel results in a shortening of cardiac action potential duration.

7. The method of claim 1, wherein the recombinant adenovirus further comprises nucleic acid sequences comprising:
   i) at least one nucleic acid sequence comprising a site-specific DNA recombinase recognition site, and
   ii) at least one nucleic acid sequence providing an essential adenovirus function,
   wherein said sequences are operably linked with the nucleic acid sequence encoding the GEM protein.

8. The method of claim 7, wherein the recombinase is Cre or Flp.

9. The method of claim 7, wherein the recombinant adenovirus further comprises the following nucleic acid sequences as operably linked components:
   i) a first inverted terminal repeat sequence (ITR),
   ii) a first lox P site,
   iii) an adenovirus packaging sequence ($\Psi$),
   iv) a strong viral promoter,
   v) a polyadenylation signal (An),
   vi) a second lox P site, and
   vii) a second inverted terminal repeat sequence (ITR).

10. The method of claim 9, wherein the recombinant adenovirus further comprises an internal ribosome entry site (IRES).

11. The method of claim 10, wherein the recombinant adenovirus further comprises at lease one adenovirus early gene (E2 and E4) or a functional fragment thereof.

12. The method of claim 11, wherein the recombinant adenovirus further comprises a sequence encoding a selectable marker.

13. The method of claim 12, wherein the selectable marker is an in-frame fusion encoding a fluorescent, phosphorescent, or chemiluminescent protein.

14. The method of claim 7, wherein the recombinant adenovirus further comprises the following operably linked components in sequence:
   i) a first inverted terminal repeat sequence (ITR),
   ii) a first lox P site,
   iii) a packaging sequence ($\Psi$),
   iv) a cytomegalovirus promoter,
   v) a sequence encoding the GEM protein,
   vi) an internal ribosome entry site (IRES),
   vii) a polyadenylation signal (An),
   viii) a second lox P site,
   ix) a sequence comprising the adenovirus early region 2 and early region 4 genes, and
   x) a second inverted terminal repeat sequence (ITR).

15. The method of claim 14, wherein the recombinant adenovirus has a size of between about 35 kilobases to about 40 kilobases.

16. The method of claim 1, wherein the recombinant adenovirus is administered to the mammal at a titre of between about $10^8$ to $10^{12}$ p.f.u.

17. The method of claim 1, wherein expression of the GEM protein can be detected from about 12 hours after contacting.

18. The method of claim 17, wherein the expression of the GEM protein is sufficient to partially block the activity of an L-type calcium channel from about 24 hours after contacting.

19. The method of claim 17, wherein the expression of the GEM protein is sufficient to partially block the activity of an L-type calcium channel from about 24 hours to about 1 month after contacting.

20. The method of claim 1, wherein the pre-determined region of excitable cardiac cells is further defined as the atrioventricular (AV) node, sinoatrial (SA) node, or the Purkinje fibers (Bundle of His).

21. A method for blocking activity of a calcium channel in a predetermined region of excitable cardiac cells in a mammal, the method comprising:
   contacting directly the excitable cardiac cells with a recombinant adenovirus comprising a nucleic acid encoding a GEM protein having the amino acid sequence according to SEQ ID NO: 1, under conditions sufficient for the excitable cardiac cells to express the GEM protein,
   wherein the GEM protein is expressed at a level sufficient to partially block activity of the calcium channel,
   wherein the calcium channel is a an L-type calcium channel;
   wherein the pre-determined region of excitable cardiac cells is in the ventricular or atrial chamber of the heart, and
   wherein the L-type calcium channel activity is reduced in a pre-determined region of an atrium.

22. The method of claim 1, wherein the mammal is a rodent.

23. The method of claim 1, wherein the mammal is a guinea pig.

24. The method of claim 1, wherein the mammal is a mouse.

25. The method of claim 1, wherein the mammal is a primate.

26. The method of claim 1, wherein the mammal is a human.

27. The method of claim 1, wherein the mammal is a pig.

* * * * *

SEQUENCE LISTING

<160> NUMBER OF SEQ ID NOS: 1

<210> SEQ ID NO 1
<211> LENGTH: 296
<212> TYPE: PRT
<213> ORGANISM: Homo sapiens

<400> SEQUENCE: 1

```
Met Thr Leu Asn Asn Val Thr Met Arg Gln Gly Thr Val Gly Met Gln
  1               5                  10                  15

Pro Gln Gln Gln Arg Trp Ser Ile Pro Ala Asp Gly Arg His Leu Met
             20                  25                  30

Val Gln Lys Glu Pro His Gln Tyr Ser His Arg Asn Arg His Ser Ala
         35                  40                  45

Thr Pro Glu Asp His Cys Arg Arg Ser Trp Ser Ser Asp Ser Thr Asp
     50                  55                  60

Ser Val Ile Ser Ser Glu Ser Gly Asn Thr Tyr Tyr Arg Val Val Leu
 65                  70                  75                  80

Ile Gly Glu Gln Gly Val Gly Lys Ser Thr Leu Ala Asn Ile Phe Ala
                 85                  90                  95

Gly Val His Asp Ser Met Asp Ser Asp Cys Glu Val Leu Gly Glu Asp
                100                 105                 110

Thr Tyr Glu Arg Thr Leu Met Val Asp Gly Glu Ser Ala Thr Ile Ile
            115                 120                 125

Leu Leu Asp Met Trp Glu Asn Lys Gly Glu Asn Glu Trp Leu His Asp
        130                 135                 140

His Cys Met Gln Val Gly Asp Ala Tyr Leu Ile Val Tyr Ser Ile Thr
145                 150                 155                 160

Asp Arg Ala Ser Phe Glu Lys Ala Ser Glu Leu Arg Ile Gln Leu Arg
                165                 170                 175

Arg Ala Arg Gln Thr Glu Asp Ile Pro Ile Ile Leu Val Gly Asn Lys
            180                 185                 190

Ser Asp Leu Val Arg Cys Arg Glu Val Ser Val Ser Glu Gly Arg Ala
        195                 200                 205

Cys Ala Val Val Phe Asp Cys Lys Phe Ile Glu Thr Ser Ala Ala Val
210                 215                 220

Gln His Asn Val Lys Glu Leu Phe Glu Gly Ile Val Arg Gln Val Arg
225                 230                 235                 240

Leu Arg Arg Asp Ser Lys Glu Lys Asn Glu Arg Arg Leu Ala Tyr Gln
                245                 250                 255

Lys Arg Lys Glu Ser Met Pro Arg Lys Ala Arg Arg Phe Trp Gly Lys
            260                 265                 270

Ile Val Ala Lys Asn Asn Lys Asn Met Ala Phe Lys Leu Lys Ser Lys
        275                 280                 285

Ser Cys His Asp Leu Ser Val Leu
    290                 295
```